US012667336B2

(12) United States Patent　　(10) Patent No.:　US 12,667,336 B2

Okada　　(45) Date of Patent:　Jun. 30, 2026

(54) ULTRASOUND DIAGNOSTIC APPARATUS AND DISPLAY METHOD OF ULTRASOUND DIAGNOSTIC APPARATUS

(71) Applicant: FUJIFILM Corporation, Tokyo (JP)

(72) Inventor: Yuto Okada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 101 days.

(21) Appl. No.: 18/296,422

(22) Filed: Apr. 6, 2023

(65) Prior Publication Data

US 2023/0240655 A1　　Aug. 3, 2023

Related U.S. Application Data

(63) Continuation of application No. PCT/JP2021/036795, filed on Oct. 5, 2021.

(30) Foreign Application Priority Data

Oct. 16, 2020　(JP) ................................. 2020-174580

(51) Int. Cl.
*A61B 8/00*　　(2006.01)

(52) U.S. Cl.
CPC .............. *A61B 8/463* (2013.01); *A61B 8/465* (2013.01)

(58) Field of Classification Search
CPC ......... A61B 8/463; A61B 8/465; A61B 8/461; A61B 8/467
See application file for complete search history.

(56) References Cited

U.S. PATENT DOCUMENTS

2014/0221836 A1 *　8/2014　Takeda ................... A61B 8/463
　　　　　　　　　　　　　　　　　　　　　600/443
2016/0206283 A1　7/2016　Ota
　　　　　(Continued)

FOREIGN PATENT DOCUMENTS

CN　　110946615 A　　4/2020
JP　　2014-150804 A　　8/2014
　　　　(Continued)

OTHER PUBLICATIONS

WO2020024255A1 (Shenzhen Mindray Biomedical Electronics Co Ltd). Translated by Espacenet. Jun. 2, 2020, [ retrieved Sep. 25, 2024]. (Year: 2020).*

(Continued)

*Primary Examiner* — Andrew W Begeman

(74) *Attorney, Agent, or Firm* — Studebaker Brackett PLLC

(57)　　ABSTRACT

In an ultrasound diagnostic apparatus and a display method of the ultrasound diagnostic apparatus, a first display region including an ultrasound image of one lung of a subject captured using an ultrasound probe, a second display region including a plurality of examination location selection buttons for selecting one examination location as an examination target location from among a plurality of examination locations in the one lung, and a third display region where a first display screen including a freeze button is displayed are displayed on a monitor. In a case where the freeze button is selected, instead of the first display screen, a second display screen including a plurality of diagnostic finding buttons corresponding to a plurality of predetermined diagnostic findings is displayed in the third display region.

20 Claims, 16 Drawing Sheets

(56)     References Cited

U.S. PATENT DOCUMENTS

| 2017/0086790 A1 | 3/2017 | Halmann et al. |
| 2019/0355149 A1 | 11/2019 | Avendi et al. |
| 2020/0205783 A1* | 7/2020 | Shiran .................. A61B 8/468 |
| 2021/0145401 A1 | 5/2021 | Lin et al. |

FOREIGN PATENT DOCUMENTS

| JP | 2016-131763 A | 7/2016 |
| JP | 2019-508072 A | 3/2019 |
| JP | 2019-535346 A | 12/2019 |
| WO | WO-2020024255 A1 * | 2/2020 |

OTHER PUBLICATIONS

The extended European search report issued by the European Patent Office on Mar. 1, 2024, which corresponds to European Patent Application No. 21879924.5.

International Search Report issued in PCT/JP2021/036795; mailed Dec. 21, 2021.

International Preliminary Report On Patentability (Chapter I) and Written Opinion of the International Searching Authority issued in PCT/JP2021/036795; issued Apr. 13, 2023.

Communication pursuant to Article 94(3) EPC issued by the European Patent Office on Feb. 6, 2025, which Corresponds to European Patent Application No. 21879924.5-1122 and is related to U.S. Appl. No. 18/296,422.

* cited by examiner

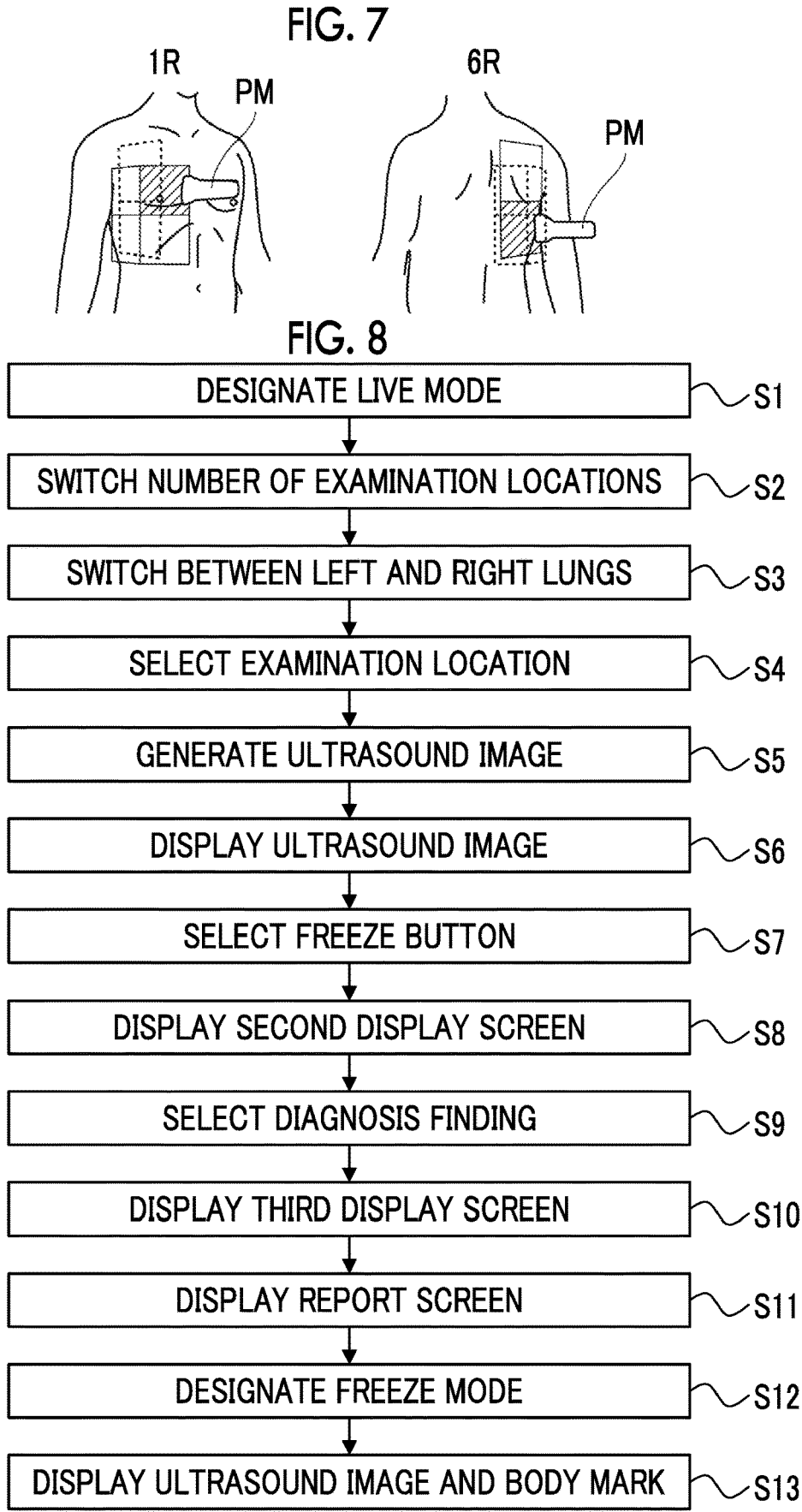

DESIGNATE LIVE MODE — S1

SWITCH NUMBER OF EXAMINATION LOCATIONS — S2

SWITCH BETWEEN LEFT AND RIGHT LUNGS — S3

SELECT EXAMINATION LOCATION — S4

GENERATE ULTRASOUND IMAGE — S5

DISPLAY ULTRASOUND IMAGE — S6

SELECT FREEZE BUTTON — S7

DISPLAY SECOND DISPLAY SCREEN — S8

SELECT DIAGNOSIS FINDING — S9

DISPLAY THIRD DISPLAY SCREEN — S10

DISPLAY REPORT SCREEN — S11

DESIGNATE FREEZE MODE — S12

DISPLAY ULTRASOUND IMAGE AND BODY MARK — S13

FIG. 9

4 AREAS FOR ONE SIDE

6 AREAS FOR ONE SIDE

R1

U

B1

B3

1R

B2    R↔L

R2

2R    3R

BM

4R

R3

C2        C1        C3

ULTRASOUND DIAGNOSTIC APPARATUS AND DISPLAY METHOD OF ULTRASOUND DIAGNOSTIC APPARATUS

CROSS-REFERENCE TO RELATED APPLICATIONS

This application is a Continuation of PCT International Application No. PCT/JP2021/036795 filed on Oct. 5, 2021, which claims priority under 35 U.S.C. § 119(a) to Japanese Patent Application No. 2020-174580 filed on Oct. 16, 2020. The above applications are hereby expressly incorporated by reference, in their entirety, into the present application.

BACKGROUND OF THE INVENTION

1. Field of the Invention

The present invention relates to an ultrasound diagnostic apparatus and a display method of the ultrasound diagnostic apparatus which switch and display a display screen in a case of capturing an ultrasound image, on a limited display region of a monitor.

2. Description of the Related Art

In the related art, in the medical field, an ultrasound diagnostic apparatus using an ultrasound image has been put to practical use. In general, the ultrasound diagnostic apparatus includes an ultrasound probe with a built-in transducer array, and a diagnostic apparatus main body connected to the ultrasound probe. In the ultrasound diagnostic apparatus, an ultrasound image is generated by transmitting an ultrasound beam from the ultrasound probe toward the subject, receiving an ultrasound echo from the subject by the ultrasound probe, and electrically processing a reception signal thereof.

In recent years, portable and handheld ultrasound diagnostic apparatuses have been developed, as well as stationary ultrasound diagnostic apparatuses. In the portable ultrasound diagnostic apparatus, the diagnostic apparatus main body is realized by a laptop terminal device. On the other hand, in the handheld ultrasound diagnostic apparatus, the diagnostic apparatus main body is realized by a handheld terminal device such as a smartphone or a tablet personal computer (PC), and an ultrasound diagnosis application program running on the terminal device.

Here, there are JP2016-131763A and JP2019-508072A as the documents in the related art that are references for the present invention.

JP2016-131763A discloses an ultrasound diagnostic apparatus which superimposes and displays an examination location selection image displaying a left hand image including a plurality of examination location marks corresponding to a plurality of examination locations, a body mark having a probe mark at a designated left hand examination location corresponding to the examination location mark, on a left hand ultrasound diagnosis screen. JP2016-131763A discloses that a finger joint of the left hand is designated as the examination location by selecting the examination location mark. Further, JP2016-131763A discloses that the ultrasound diagnosis screen includes a freeze button.

JP2019-508072A discloses a medical imaging system configured to obtain an image with various annotations by superimposing descriptive labels on a target anatomical object and/or surrounding additional anatomical objects/tissues on a real-time two-dimensional ultrasound image.

SUMMARY OF THE INVENTION

However, JP2016-131763A and JP2019-508072A do not disclose that a plurality of display screens for operating the ultrasound diagnostic apparatus are switched by efficiently arranging various buttons, display screens, and the like on a monitor with a limited display region. In other words, in the ultrasound diagnostic apparatus in the related art, it is not possible to operate the ultrasound diagnostic apparatus by efficiently using the limited display region of the monitor by switching the plurality of display screens.

An object of the present invention is to provide an ultrasound diagnostic apparatus and a display method of the ultrasound diagnostic apparatus which can display a display screen for operating the ultrasound diagnostic apparatus by efficiently using a display screen of a monitor with a limited display region.

In order to achieve the object, an aspect of the present invention provides an ultrasound diagnostic apparatus including an ultrasound probe; and a diagnostic apparatus main body connected to the ultrasound probe, in which the diagnostic apparatus main body includes a display control unit, and a monitor, the display control unit displays, on the monitor, a first display region including an ultrasound image of one lung of a subject captured using the ultrasound probe, a second display region including a plurality of examination location selection buttons for selecting one examination location as an examination target location from among a plurality of examination locations in the one lung, and a third display region where a first display screen including a freeze button is displayed, and the display control unit displays, in a case where the freeze button is selected, instead of the first display screen, a second display screen including a plurality of diagnostic finding buttons corresponding to a plurality of predetermined diagnostic findings in the third display region.

Here, it is preferable that, in a case where a third display screen switching button is selected, the display control unit displays, instead of the second display screen, a third display screen for selecting an ultrasound image of one frame from among ultrasound images of a plurality of frames captured during a certain past period up to a time point of selecting the freeze button in the third display region.

It is preferable that the plurality of diagnostic finding buttons have a design according to a type of the ultrasound probe connected to the diagnostic apparatus main body, and in a case where the type of the ultrasound probe connected to the diagnostic apparatus main body is changed, the display control unit displays, instead of the plurality of diagnostic finding buttons being displayed, the second display screen including a plurality of diagnostic finding buttons with a design according to the changed type of the ultrasound probe in the third display region.

It is preferable that one diagnostic finding selected from among the plurality of diagnostic findings is input for each examination location by one diagnostic finding button selected from among the plurality of diagnostic finding buttons.

It is preferable that the display control unit displays the ultrasound image, and the diagnostic finding input for the ultrasound image, in the first display region.

It is preferable that, in a case where a report screen switching button is selected, the display control unit displays a report screen collectively including the diagnostic findings input for the plurality of examination locations, in a display region including the first display region, the second display region, and the third display region.

It is preferable that the report screen includes a diagnostic finding body mark, and the diagnostic finding body mark includes a schematic diagram of a human body, and an examination location mark that is displayed on the schematic diagram in a superimposed manner, and indicates the examination location.

It is preferable that the display control unit further displays a body mark indicating the examination target location in the second display region.

It is preferable that at least one of the plurality of diagnostic findings includes any one of diagnostic findings of B-lines, consolidation, normal, or no lung sliding.

Another aspect of the present invention provides a display method of an ultrasound diagnostic apparatus including an ultrasound probe, and a diagnostic apparatus main body connected to the ultrasound probe, the diagnostic apparatus main body including a monitor, and the display method includes displaying, on the monitor, a first display region including an ultrasound image of one lung of a subject captured using the ultrasound probe, a second display region including a plurality of examination location selection buttons for selecting one examination location as an examination target location from among a plurality of examination locations in the one lung, and a third display region where a first display screen including a freeze button is displayed; and displaying, in a case where the freeze button is selected, instead of the first display screen, a second display screen including a plurality of diagnostic finding buttons corresponding to a plurality of predetermined diagnostic findings in the third display region.

According to the present invention, it is possible to display a display region for operating the ultrasound diagnostic apparatus by efficiently using a display screen of a monitor with a limited display region by switching the first display screen to the second display screen and displaying the second display screen in the third display region.

BRIEF DESCRIPTION OF THE DRAWINGS

FIG. 7 is a conceptual diagram of an embodiment illustrating body marks in a case where an examination location mark corresponding to an examination location on a back side of a schematic diagram is displayed on a front side of the schematic diagram by allowing the schematic diagram to be transparent.

FIG. 8 is a flowchart of an embodiment illustrating an operation of an ultrasound diagnostic apparatus of the present invention.

FIG. 9 is a conceptual diagram of an embodiment illustrating an examination location number switching screen.

DESCRIPTION OF THE PREFERRED EMBODIMENTS

Hereinafter, an ultrasound diagnostic apparatus and a display method of the ultrasound diagnostic apparatus according to the present invention will be described in detail on the basis of preferred embodiments illustrated in the accompanying drawings.

Figure 1:
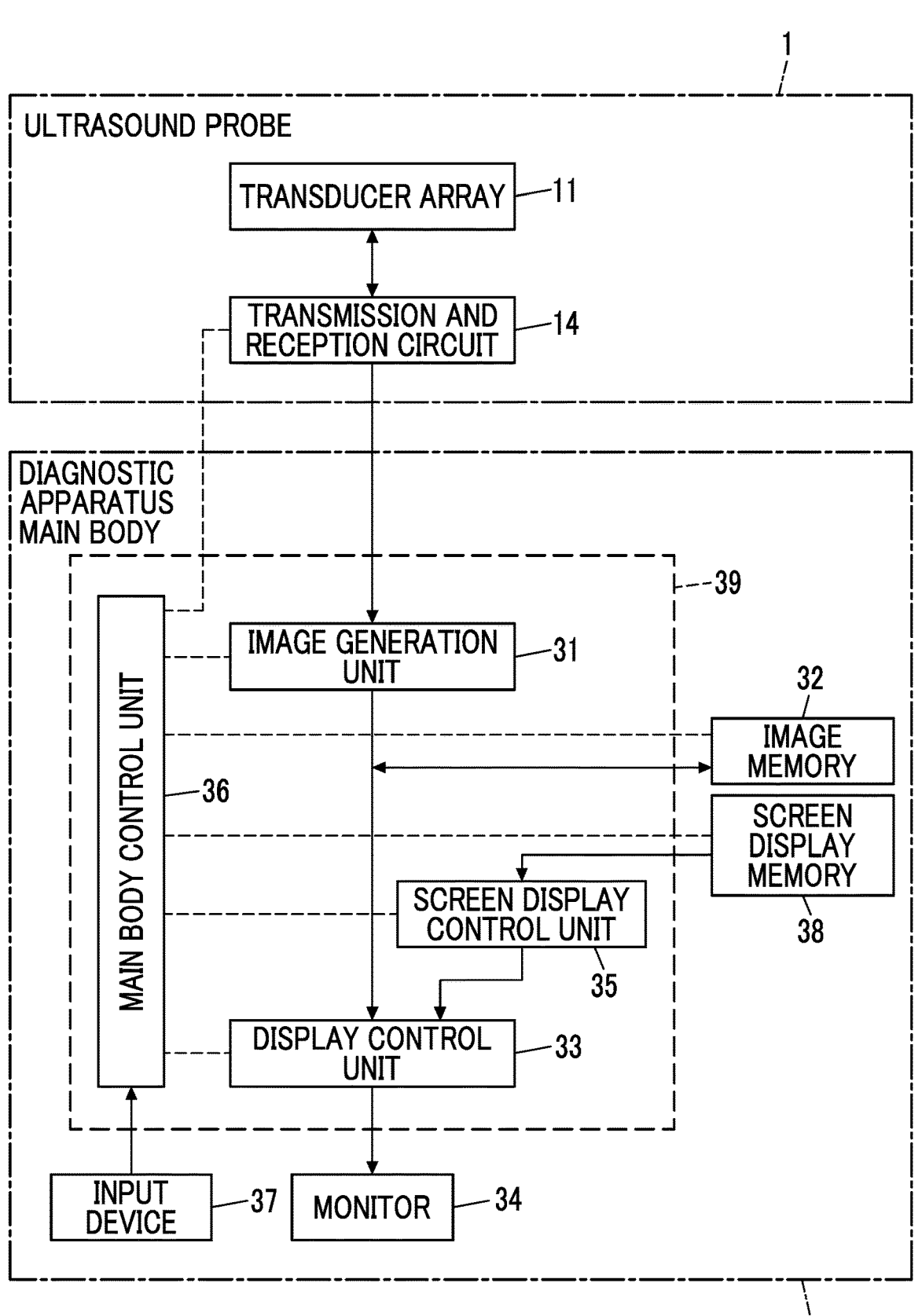
FIG. 1 is a block diagram of an embodiment illustrating a configuration of an ultrasound diagnostic apparatus of the present invention.

FIG. 1 is a block diagram of an embodiment illustrating a configuration of an ultrasound diagnostic apparatus of the present invention. The ultrasound diagnostic apparatus illustrated in FIG. 1 includes an ultrasound probe 1, and a diagnostic apparatus main body 3 connected to the ultrasound probe 1. The ultrasound diagnostic apparatus of the present embodiment is realized by the handheld diagnostic apparatus main body 3 such as a smartphone or a tablet PC, and an ultrasound diagnosis application program running on the diagnostic apparatus main body 3.

The ultrasound probe 1 scans a subject, one lung of the subject in the present embodiment, using an ultrasound beam, and outputs a sound ray signal corresponding to an ultrasound image. As illustrated in FIG. 1, the ultrasound probe 1 includes a transducer array 11, and a transmission and reception circuit 14. The transducer array 11 and the transmission and reception circuit 14 are bidirectionally connected to each other. Further, a main body control unit 36 to be described later is connected to the transmission and reception circuit 14.

The transducer array 11 includes a plurality of ultrasonic transducers arranged in a one-dimensional or two-dimensional manner. According to a drive signal supplied from the transmission and reception circuit 14, each of the transducers transmits an ultrasonic wave and receives a reflected wave (ultrasound echo) from the subject to output an analog reception signal.

For example, each transducer is formed by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
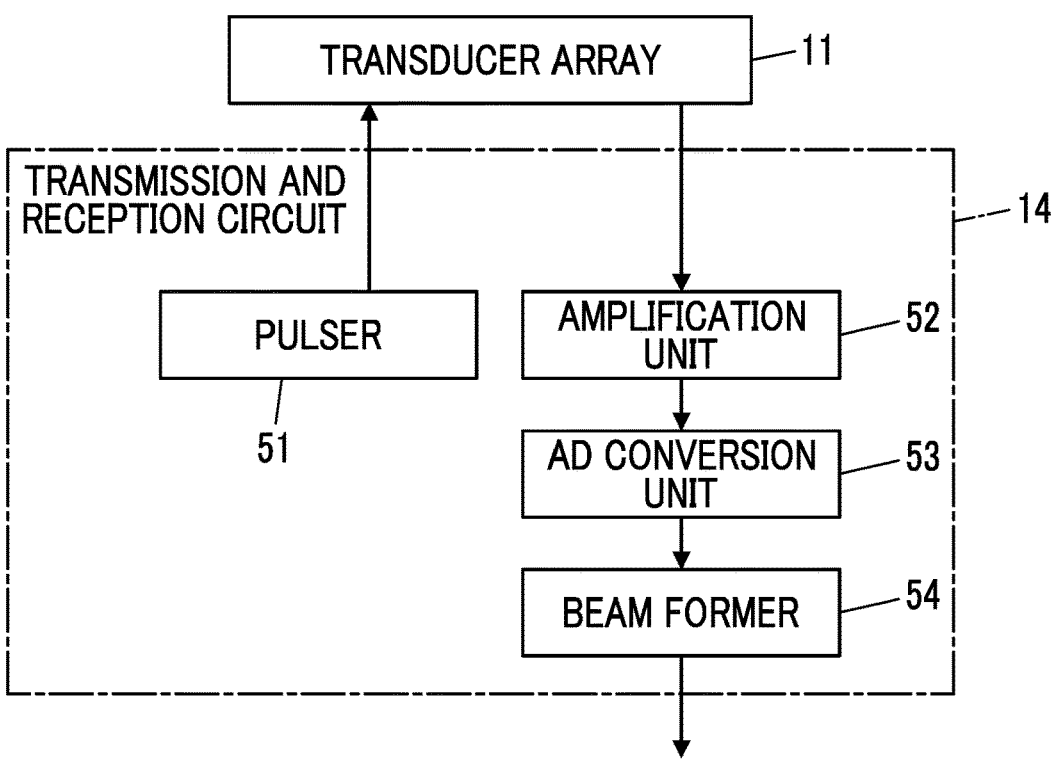
FIG. 2 is a block diagram of an embodiment illustrating a configuration of a transmission and reception circuit.

The transmission and reception circuit 14 causes the transducer array 11 to transmit the ultrasonic wave, and performs reception focusing processing on the reception signal output from the transducer array 11 that has received the ultrasound echo to generate a sound ray signal, under the control of the main body control unit 36. As illustrated in FIG. 2, the transmission and reception circuit 14 includes a pulser 51 connected to the transducer array 11, and an amplification unit 52, an analog digital (AD) conversion unit 53, and a beam former 54 that are sequentially connected in series from the transducer array 11.

The pulser 51 includes, for example, a plurality of pulse generators, and the pulser 51 adjusts the amount of delay of each drive signal so that ultrasonic waves transmitted from the plurality of transducers of the transducer array 11 form an ultrasound beam on the basis of a transmission delay pattern selected by the main body control unit 36, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. Each transducer constituting the transducer array 11 expands and contracts by receiving the ultrasound echo propagating toward the transducer array 11 in this manner, to generate the reception signal that is an electric signal, and outputs the reception signal to the amplification unit 52.

The amplification unit 52 amplifies the signals input from each transducer constituting the transducer array 11, and transmits the amplified signals to the AD conversion unit 53. The AD conversion unit 53 converts the analog signal transmitted from the amplification unit 52 into digital reception data, and outputs the reception data to the beam former 54.

The beam former 54 performs so-called reception focusing processing in which addition is performed by giving delays to respective pieces of the reception data converted by the AD conversion unit 53 according to a sound speed distribution or a sound speed set on the basis of a reception delay pattern selected by the main body control unit 36. Through the reception focusing processing, a sound ray signal in which each piece of the reception data converted by the AD conversion unit 53 is phased and added and the focus of the ultrasound echo is narrowed is generated.

Next, the diagnostic apparatus main body 3 displays various buttons for operating the ultrasound diagnostic apparatus, display screens, and the like in addition to the ultrasound image based on the sound ray signal generated by the ultrasound probe 1. As illustrated in FIG. 1, the diagnostic apparatus main body 3 includes an image generation unit 31, an image memory 32, a screen display memory 38, a screen display control unit 35, a display control unit 33, the main body control unit 36, a monitor (display device) 34, and an input device 37.

The image generation unit 31 is connected to the transmission and reception circuit 14 of the ultrasound probe 1, and the display control unit 33 and the monitor 34 are sequentially connected in series to the image generation unit 31. The image memory 32 is bidirectionally connected to the image generation unit 31. The screen display control unit 35 is connected to the screen display memory 38, and the display control unit 33 is connected to the screen display control unit 35. The main body control unit 36 is connected to the transmission and reception circuit 14, the image generation unit 31, the display control unit 33, the image memory 32, the screen display memory 38, and the screen display control unit 35 that are described above, and the input device 37 is connected to the main body control unit 36.

Figure 3:
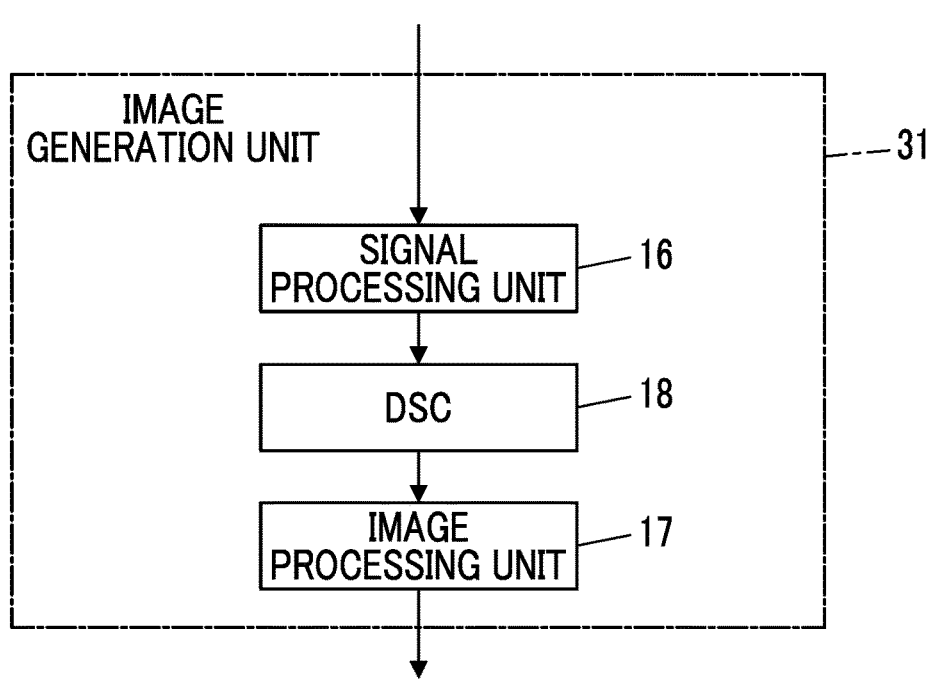
FIG. 3 is a block diagram of an embodiment illustrating a configuration of an image generation unit.

The image generation unit 31 generates the ultrasound image (ultrasound image signal) on the basis of the sound ray signal generated by the transmission and reception circuit 14 under the control of the main body control unit 36. As illustrated in FIG. 3, the image generation unit 31 has a configuration in which a signal processing unit 16, a digital scan converter (DSC) 18, and an image processing unit 17 are sequentially connected in series.

The signal processing unit 16 generates image information data corresponding to the ultrasound image on the basis of the sound ray signal generated by the transmission and reception circuit 14. More specifically, the signal processing unit 16 generates the image information data representing tomographic image information regarding tissues inside the subject, by performing envelope detection processing after signal processing, for example, correcting the attenuation of the sound ray signal generated by the beam former 54 of the transmission and reception circuit 14, which is caused by the propagation distance according to the depth of the reflection position of the ultrasonic wave.

The DSC 18 raster-converts the image information data generated by the signal processing unit 16 into an image signal according to a normal television signal scanning method.

The image processing unit 17 performs various kinds of image processing such as brightness correction, gradation correction, sharpness correction, image size correction, refresh rate correction, scanning frequency correction, and color correction according to a display format of the monitor 34, on the image signal input from the DSC 18 to generate the ultrasound image (ultrasound image signal), and then outputs the generated ultrasound image to the display control unit 33 and the image memory 32.

In the present embodiment, the image generation unit 31 generates an ultrasound image of one lung of the subject on the basis of the sound ray signal generated by the transmission and reception circuit 14 from the reception signal obtained by performing transmission and reception of the ultrasound beams with respect to the one lung of the subject using the ultrasound probe 1.

The image memory 32 stores ultrasound images (ultrasound image signal) of the series of a plurality of frames, which are generated for each examination location by the image generation unit 31, under the control of the main body control unit 36. More specifically, the image memory 32 saves the ultrasound image generated by the image generation unit 31 in a case where a live mode is designated. Further, in the image memory 32, as described later, the ultrasound image, and the examination location, the body mark, the diagnostic findings, and the like, which correspond to the ultrasound image, are saved in association with each other.

The image memory 32 has a memory capacity for saving ultrasound images of several tens to several hundreds of frames in a case where ultrasound images for several seconds to several tens of seconds, for example, ultrasound images of 30 frames for one second are captured. The image memory 32 is a ring buffer. Thus, in a case where the ultrasound images of a plurality of past frames for the number of frames corresponding to the memory capacity are saved in the image memory 32, instead of the ultrasound image of the oldest frame, the ultrasound image of the latest frame is sequentially saved in the image memory 32. In this manner, the ultrasound images of the past frames for the number of frames corresponding to the memory capacity, from the ultrasound image of the latest frame are always saved in the image memory 32.

Here, the live mode is a mode in which the ultrasound images (video) captured at a certain frame rate are sequentially displayed (real time display).

In contrast to the live mode, a freeze mode is a mode in which the ultrasound images (video) captured in a case where the live mode is designated are saved in the image memory 32 and the ultrasound image (static image) of any one frame is read out and displayed from the ultrasound images (video) of the plurality of past frames saved in the image memory 32.

The screen display memory 38 stores data such as various buttons, various body marks, and various display screens, which will be described later. The data is read out from the screen display memory 38, and is supplied to the screen display control unit 35, under the control of the main body control unit 36.

Here, as the image memory 32 and the screen display memory 38, recording media such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The screen display control unit 35 outputs the data such as a button, a body mark, and a display screen, which correspond to a user' instruction input from the input device 37, from among the pieces of data such as various buttons, various buttons, and various display screens which are read out from the screen display memory 38, under the control of the main body control unit 36. The data such as a button, a body mark, and a display screen, which is output from the screen display control unit 35, is supplied to the display control unit 33. Further, the screen display control unit 35 creates a report screen to be described later, on the basis of the diagnostic findings read out from the image memory 32, and the data such as various buttons, various body marks, and various display screens which are read out from the screen display memory 38.

The display control unit 33 displays various kinds of information on the monitor 34 under the control of the main body control unit 36. The display control unit 33 performs predetermined processing on the ultrasound image held in the image memory 32, and displays the processed ultrasound image on the monitor 34. In addition, the display control unit 33 displays the button, the body mark, the display screen, and the like, which correspond to the user's instruction input from the input device 37, on the monitor 34 on the basis of the data such as the button, the body mark, and the display screen, which is supplied from the screen display control unit 35.

The main body control unit 36 controls each unit of the diagnostic apparatus main body 3 on the basis of a program stored in advance and an instruction or the like of the user (doctor, technician, nurse, or the like who operates the ultrasound diagnostic apparatus) input from the input device 37. More specifically, the main body control unit 36 controls the transmission and reception circuit 14 to generate the sound ray signal, controls the image generation unit 31 to generate the ultrasound image on the basis of the sound ray signal, and controls the display control unit 33 to display the ultrasound image on the monitor 34. The main body control unit 36 controls the screen display control unit 35 to output the data such as the button, the body mark, and the display screen, which correspond to the user's instruction. The main body control unit 36 controls the screen display control unit 35 to display the button, the body mark, the display screen, and the like which correspond to the user's instruction, on the monitor 34.

The image generation unit 31, the display control unit 33, the screen display control unit 35, and the main body control unit 36 constitute a processor 39 for the ultrasound diagnostic apparatus.

The monitor 34 displays various kinds of information under the control of the display control unit 33. The monitor 34 displays the body mark and the like described above in addition to the ultrasound image, and various buttons and various display screens which are for operating the ultrasound diagnostic apparatus. Examples of the monitor 34 include a display device such as a liquid crystal display (LCD), and an organic electroluminescence (EL) display.

The input device 37 receives various instructions input from the user, and includes a physical key that the user presses to input various instructions, and a touch panel or the like which is provided on the display screen of the monitor 34 and through which various instructions are input by the user performing a touch operation.

Next, the display screen of the monitor 34 will be described.

Figure 4:
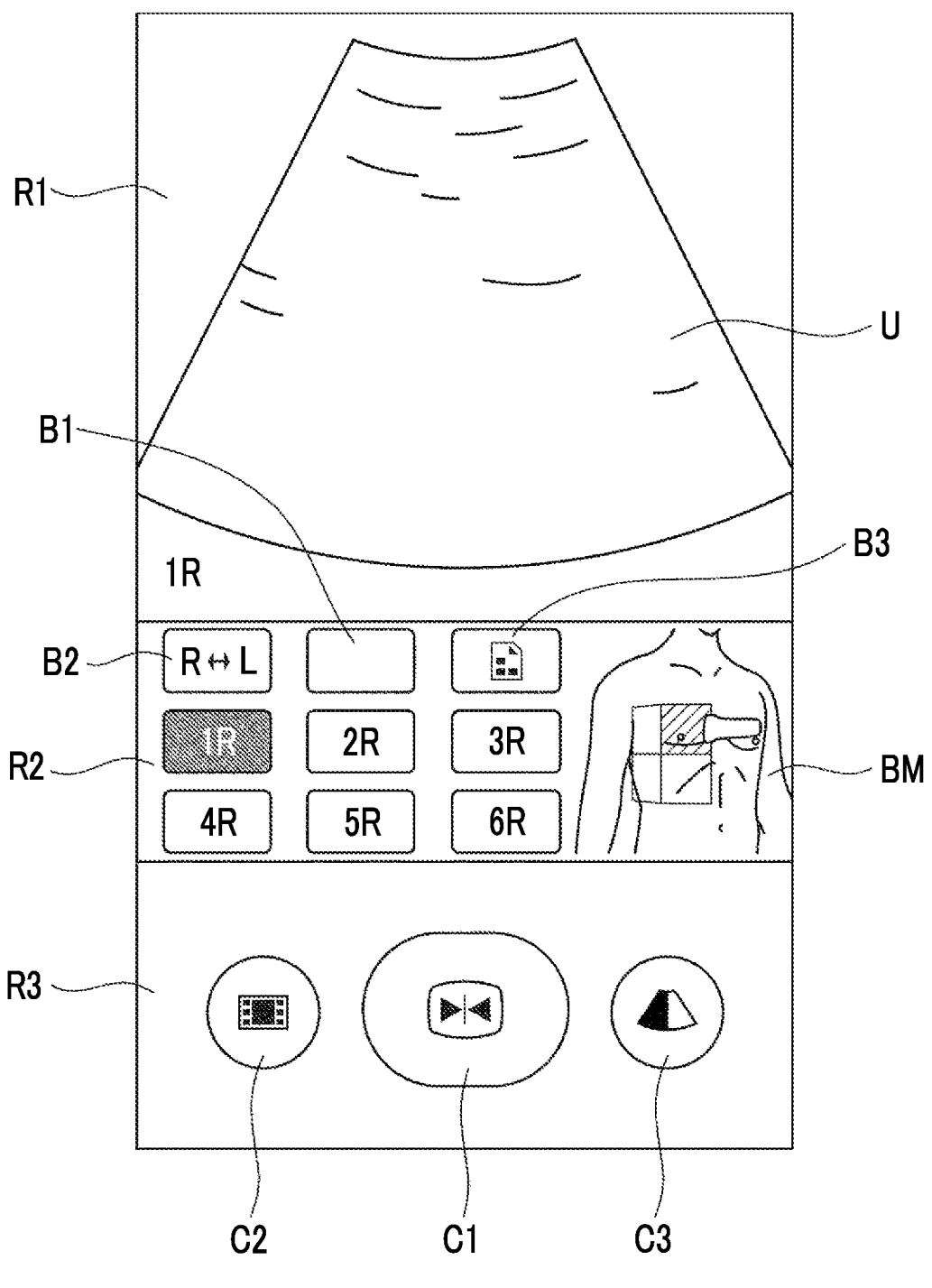
FIG. 4 is a conceptual diagram of an embodiment illustrating a display screen of a monitor of a handheld ultrasound diagnostic apparatus.

FIG. 4 is a conceptual diagram of an embodiment illustrating a display screen of a monitor of a handheld ultrasound diagnostic apparatus. In the example of FIG. 4, the display screen of the monitor 34 of the handheld ultrasound diagnostic apparatus is vertically long, and includes a first display region R1, a second display region R2, and a third display region R3.

The first display region R1 is a region where an ultrasound image U or the like of one lung of the subject captured using the ultrasound probe 1 is displayed, and is arranged in a region from the upper portion of the display screen of the monitor 34 to the upper side of the second display region R2.

In a case where the live mode is designated, in the first display region R1, the ultrasound image (video) U of the examination target location of one lung captured using the ultrasound probe 1 is displayed in real time.

In a case where the freeze mode is designated, in the first display region R1, the ultrasound image (static image) of the examination location selected by an examination location selection button to be described later, from among the plurality of ultrasound images saved in the image memory 32.

In addition, the examination location is displayed in the first display region R1. As illustrated in FIG. 4, for example, in a case where an examination location selection button 1R to be described later is selected, as the examination location, "1R" corresponding to the examination location selection button 1R is displayed at the lower left portion of the first display region R1.

The second display region R2 is a region where a report screen switching button B3, a body mark BM, and the like in addition to an examination location number switching button B1 for designating a target location to be examined or checked, a left and right switching button B2, and an examination location selection button are displayed, and is arranged in a region from the lower side of the first display region R1 to the upper side of the third display region R3, that is, between the first display region R1 and the third display region R3. In the example of FIG. 4, six examination location selection buttons 1R to 6R corresponding to predetermined six examination locations are displayed as the examination location selection button.

The examination location number switching button B1, the left and right switching button B2, the report screen switching button B3, and the examination location selection buttons 1R to 6R are arranged in a left region in the second display region R2, and the body mark BM is arranged in the right region in the second display region R2.

The examination location number switching button B1 is a button for switching the number of examination locations in one lung. In the present embodiment, the user can switch the number of examination locations to six or four by tapping and selecting the examination location number switching button B1.

Figure 5:
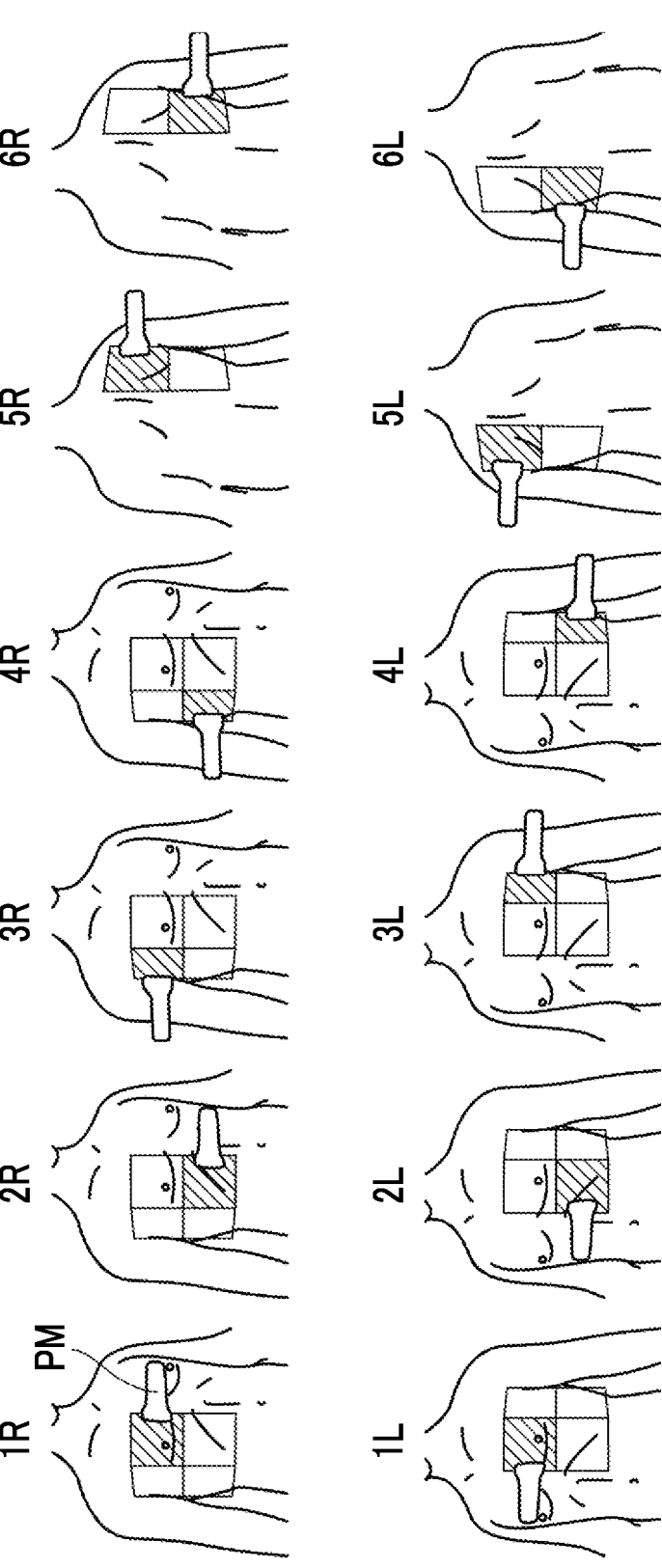
FIG. 5 is a conceptual diagram of an embodiment illustrating body marks in a case where the number of examination locations in a right lung and a left lung are six.

FIG. 5 is a conceptual diagram of an embodiment illustrating body marks in a case where the number of examination locations in a right lung and a left lung are six. As illustrated in FIG. 5, six rectangular examination location marks corresponding to six examination locations are displayed by being superimposed on the human body in the schematic diagram of the body mark BM of the right lung. In the following description, six examination locations and six examination location marks corresponding to six examination location selection buttons 1R to 6R are also expressed as examination locations 1R to 6R and examination location marks 1R to 6R. In the present embodiment, among six examination location marks 1R to 6R, the examination location marks 1R to 4R corresponding to the examination locations on the front side of the right lung of the human body in the schematic diagram are displayed by being superimposed on the front side of the human body in the schematic diagram, and the examination location marks 512 and 6R corresponding to the examination locations on the back side of the human body in the schematic diagram are displayed by being superimposed on the back side of the human body in the schematic diagram.

The examination location mark 1R indicates an upper right region among four examination location marks 1R to 4R displayed by being superimposed on the front side of the right lung of the human body in the schematic diagram, similarly, the examination location mark 2R indicates a lower right region, the examination location mark 3R indicates an upper left region, and the examination location mark 4R indicates a lower left region. The examination location mark 512 indicates an upper region among two examination location marks 512 and 6R displayed by being superimposed on the back side of the right lung of the human body in the schematic diagram, and similarly, the examination location mark 6R indicates a lower region. The region of the examination location mark corresponding to the examination target location is displayed in an emphasized manner by being displayed in a different color from the other examination location marks, being displayed with high brightness, or blinking without being particularly limited.

A probe mark PM is displayed in an orientation and at a position pointing within the region of the examination location mark corresponding to the examination target location. For example, in a case where the examination target location is the examination location 1R, the probe mark PM is displayed in an orientation and at a position pointing within the region of the examination location mark 1R.

The same applies to the body marks BM of the left lung illustrated in FIG. 5.

Figure 6:
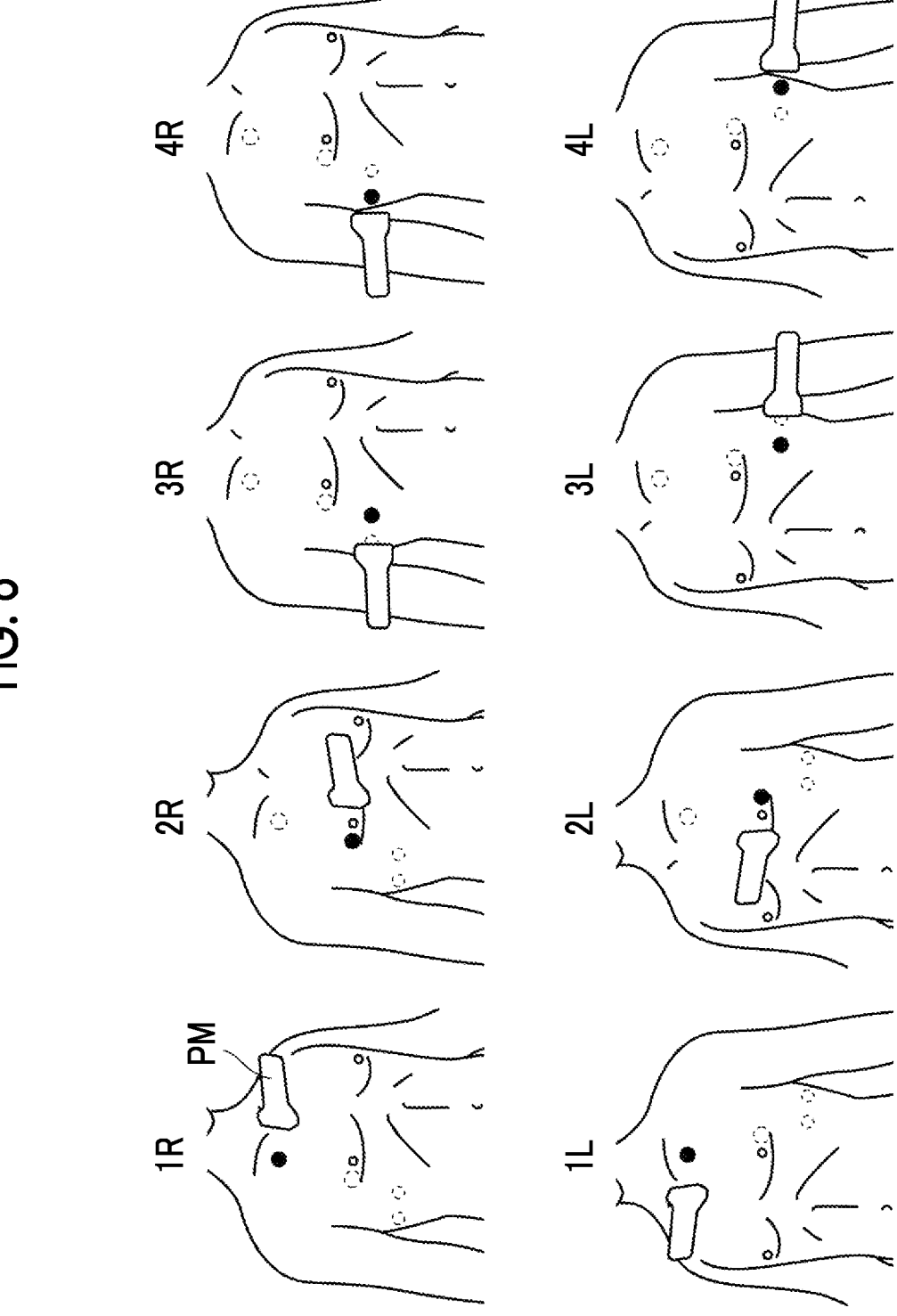
FIG. 6 is a conceptual diagram of an embodiment illustrating body marks in a case where the number of examination locations in a right lung and a left lung are four.

FIG. 6 is a conceptual diagram of an embodiment illustrating body marks in a case where the number of examination locations in a right lung and a left lung are four. As illustrated in FIG. 6, four pinpoint examination location marks corresponding to four examination locations are displayed by being superimposed on the human body in the schematic diagram of the body mark BM of the right lung. Similarly, four examination locations and four examination location marks corresponding to four examination location selection buttons 1R to 4R are also expressed as examination locations 1R to 4R and examination location marks 1R to 4R. In the present embodiment, four examination location marks 1R to 4R are displayed by being superimposed on the front side of the right lung of the human body in the schematic diagram.

The examination location mark 1R indicates an upper pinpoint among four examination location marks 1R to 4R displayed by being superimposed on the front side of the right lung of the human body in the schematic diagram, similarly, the examination location mark 2R indicates the second pinpoint from the upper side, the examination location mark 3R indicates the third pinpoint from the upper side, and the examination location mark 4R indicates a pinpoint that is at almost the same height as the examination location mark 3R, but is arranged closer to the back side than the examination location mark 3R. The pinpoint of the examination location mark corresponding to the examination target location is displayed in an emphasized manner.

The probe mark PM is displayed in an orientation and at a position pointing the pinpoint of the examination location mark corresponding to the examination target location. For example, in a case where the examination target location is the examination location 1R, the probe mark PM is displayed in an orientation and at a position pointing the pinpoint of the examination location mark 1R.

The same applies to the body marks BM of the left lung illustrated in FIG. 6.

The number of examination locations in the right lung and the left lung is not limited to six or four, can be changed to an arbitrary number such as seven, for example, and can be switched to an arbitrary number by the examination location number switching button B1. Further, as illustrated in FIGS. 5 and 6, different body marks may be used depending on the number of examination locations, or the same body mark may be used regardless of the number of examination locations. The shape of the examination location mark may be a rectangular region or a pinpoint regardless of the number of examination locations.

In addition, the human body may be displayed in a transparent schematic diagram, and the examination location mark corresponding to the examination location on the back side of the schematic diagram may be displayed on the front side of the schematic diagram through the schematic diagram. In this case, in a case where a schematic diagram indicating the front side of the human body is displayed, the examination location mark corresponding to the examination location on the back side of the human body is displayed as a dashed line or the like on the front side of the human body through the schematic diagram, as illustrated on the left side of FIG. 7. Similarly, in a case where a schematic diagram indicating the back side of the human body is displayed, the examination location mark corresponding to the examination location on the front side of the human body is displayed as a dashed line or the like on the back side of the human body through the schematic diagram, as illustrated on the right side of FIG. 7.

The left and right switching button B2 is a button for switching between the left and right lungs of the subject, in other words, a button for switching the lung as the examination target from the right lung to the left lung or from the left lung to the right lung.

The examination location selection buttons 1R to 6R are buttons for selecting one examination location as the examination target location from among six examination locations in the right lung of the subject. For example, in a case where the examination location selection button 1R is tapped and selected by the user, the selected examination location selection button 1R is displayed in an emphasized manner. The same applies to cases where the other examination location selection buttons are tapped and selected.

The report screen switching button B3 is a button for displaying the report screen collectively including the diagnostic findings input for a plurality of examination locations in both lungs, on the monitor 34.

The body mark BM illustrates the examination location and the examination target location in one lung of the subject, and includes a three-dimensional schematic diagram of the human body, a plurality of examination location marks, and the probe marks PM, as illustrated in FIGS. 5 and 6. In the present embodiment, as illustrated in FIGS. 5 and 6, the body mark BM of the right lung is displayed in the orientation corresponding to the examination location of the right lung, and the body mark BM of the left lung is displayed in the orientation corresponding to the examination location of the left lung. In other words, the body mark BM of the right lung and the body mark BM of the left lung are oriented in different directions, such as the examination locations 1R and 1L, so that the examination locations can be easily checked. Further, even in the same one lung, for example, angles for displaying the schematic diagram of the human body are changed depending on the examination locations on the front side and the back side of the lung, such as the examination locations 1R and 6R.

In the present embodiment, the schematic diagram of the human body is a schematic diagram of the torso part of the human body including the lungs, as illustrated in FIGS. 5 and 6.

A plurality of examination location marks are marks indicating a plurality of examination locations in the lung of the schematic diagram, and are displayed by being superimposed on the plurality of examination locations in the lung of the schematic diagram of the human body. The examination location mark corresponding to the examination target location among the plurality of examination location marks is displayed in an emphasized manner.

In a case where the number of examination locations is six, the plurality of examination location marks are six rectangular examination location marks 1R to 6R of the right lung or six rectangular examination location marks 1L to 6L of the left lung, as illustrated in FIG. 5. In a case where the number of examination locations is four, the plurality of examination location marks are four pinpoint examination location marks 1R to 4R of the right lung or four pinpoint examination location mark 1L to 4L of the left lung, as illustrated in FIG. 6.

The probe mark PM is a mark indicating the orientation and the position of the ultrasound probe 1 in a case of examining the examination target location, and is displayed in an orientation and at a position pointing the examination location mark corresponding to the examination target location of the human body in the schematic diagram.

The third display region R3 is displayed in a region where a second display screen or a third display screen to be described later is displayed in addition to a first display screen illustrated in FIG. 4 or instead of the first display screen, and is arranged in a region from the lower side of the second display region R2 to a lower portion of the display screen of the monitor 34.

The first display screen is a screen for performing an operation for capturing the ultrasound image U. In the first display screen, a freeze button C1, a video save button C2, and an examination parameter setting button C3 are included.

The freeze button is a button for capturing the ultrasound image (static image) U of the examination target location of the lung and saving the ultrasound image U in the image memory 32, and the video save button is a button for capturing the ultrasound image (video) U of the examination target location of the lung and saving the ultrasound image U in the image memory 32.

The examination parameter setting button is a button for setting various examination parameters including gains, scanning depths, and the like in a case of capturing the ultrasound image U.

The arrangement locations and sizes of the first display region R1, the second display region R2, and the third display region R3 are not particularly limited, and the first display region R1, the second display region R2, and the third display region R3 may be arranged in any order with any size. The arrangement locations and sizes of various buttons and the body mark BM included in the second display region R2 and the third display region R3 are not particularly limited, and various buttons and the body mark BM included in the second display region R2 and the third display region R3 may be arranged in any order with any size at any locations. Furthermore, it is not essential to display all buttons, and conversely, other buttons that are not displayed may be displayed.

Next, the operation of the ultrasound diagnostic apparatus will be described with reference to the flowchart of FIG. 8. First, the operation of the ultrasound diagnostic apparatus in the case of the live mode will be described.

In a case where the ultrasound diagnostic apparatus is powered on, the display screen including the first display region R1, the second display region R2, and the third display region R3 is displayed on the monitor 34 under the control of the display control unit 33.

First, the live mode is designated on the basis of the user's instruction input from the input device 37 (Step S1).

Figure 9:
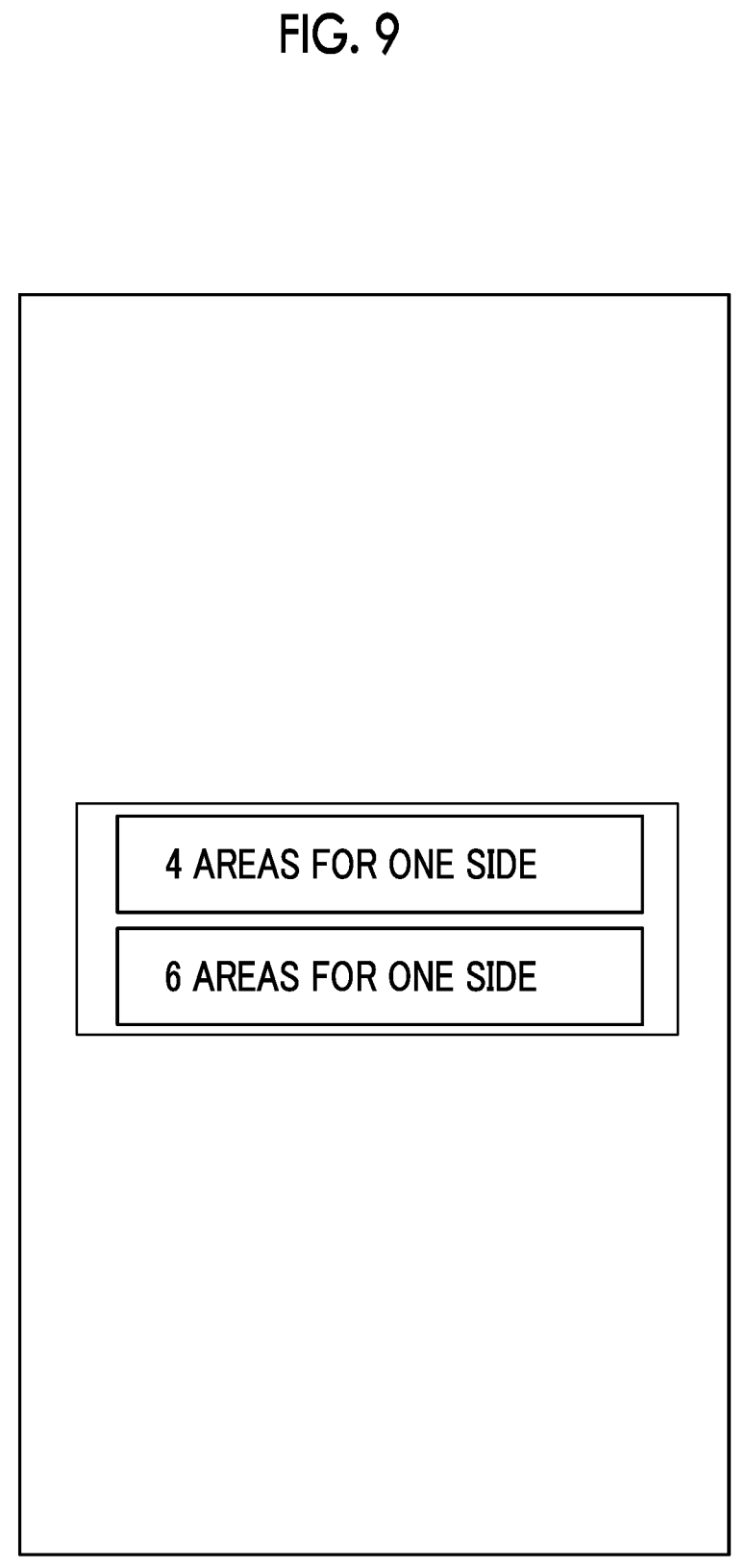

Subsequently, in a case where the user taps and selects the examination location number switching button B1 included in the second display region R2, the examination location number switching screen for switching the number of examination locations to six or four is displayed by the display control unit 33, as illustrated in FIG. 9. The user can switch the number of examination locations to six by tapping and selecting a button "6 areas for one side", and can switch the number of examination locations to four by tapping and selecting a button "4 areas for one side" (Step S2).

In a case where the number of the examination locations is switched to six, the data of the examination location selection buttons 1R to 6R and 1L to 6L corresponding to six examination locations is output to the display control unit 33 from among the data of various buttons read out from the screen display memory 38, by the screen display control unit 35. Then, as illustrated in FIG. 4, six examination location selection buttons 1R to 6R or 1L to 6L corresponding to six examination locations are displayed in the second display region R2 by the display control unit 33.

Figure 10:
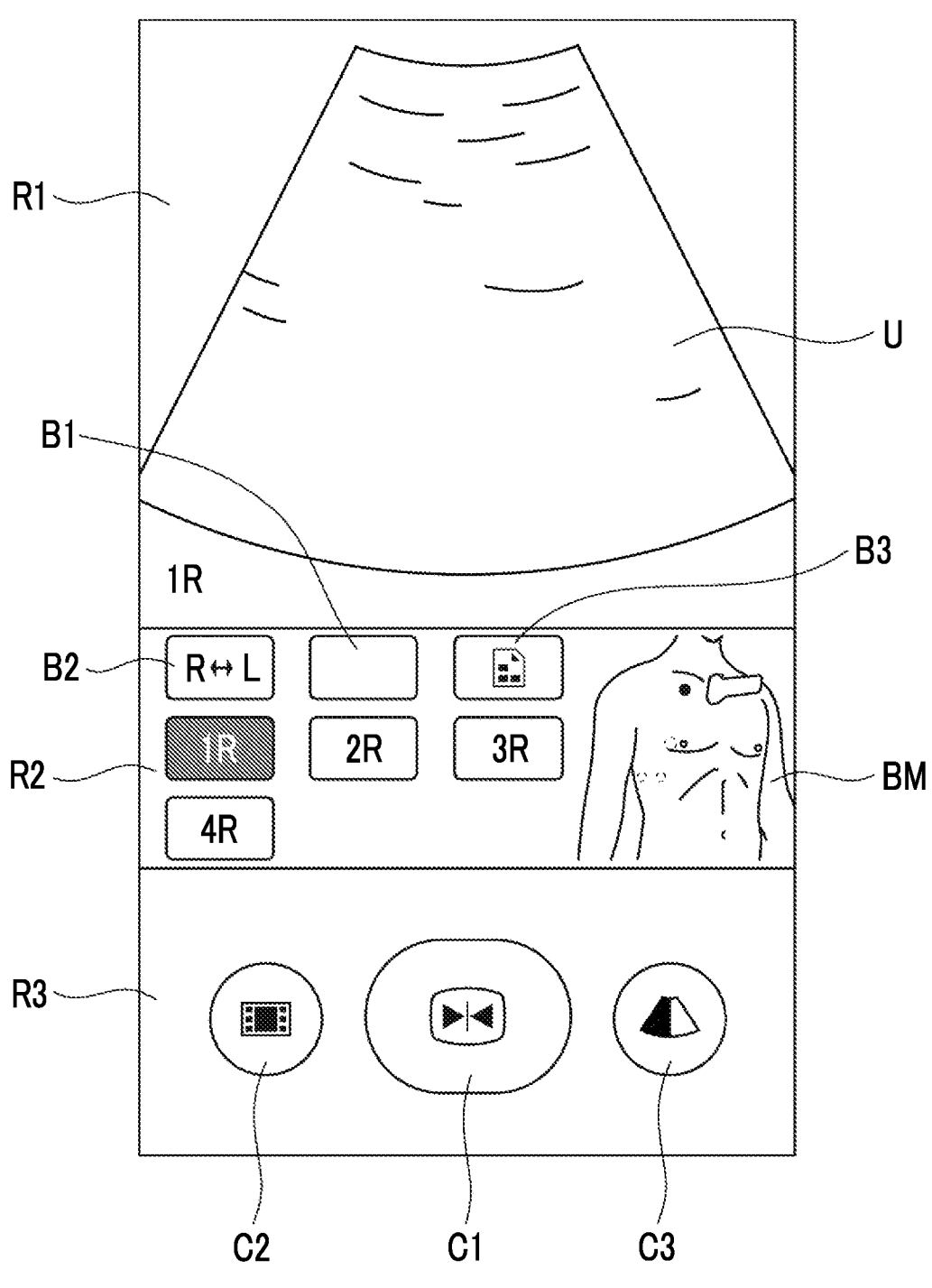
FIG. 10 is a conceptual diagram of an embodiment illustrating a display screen of a monitor in a case where the number of examination locations is four.

On the other hand, in a case where the number of the examination locations is switched to four, similarly, the data of the examination location selection buttons 1R to 4R and 1L to 4L corresponding to four examination locations is output to the display control unit 33 by the screen display control unit 35. Then, as illustrated in FIG. 10, four examination location selection buttons 1R to 4R or 1L to 4L corresponding to four examination locations are displayed in the second display region R2 by the display control unit 33.

In this manner, the examination location selection buttons of which the number matches the number of examination locations switched by the examination location number switching button B1 are displayed.

Thus, it is possible to correspond to a plurality of examination protocols for lung echo with different number of examination locations. The user can check a list of locations that require examinations by referring to the examination location selection button.

In the present embodiment, it is assumed that the number of examination locations is switched to six by the user tapping and selecting the "6 areas for one side".

Here, in a case where the examination target is a right lung, the examination location selection buttons 1R to 6R corresponding to the right lung are displayed in the second display region R2 by the display control unit 33, as illustrated in FIG. 4. In this state, in a case where the user taps and selects the left and right switching button B2, the examination target is switched from the right lung to the left lung, the data of the examination location selection buttons 1L to 6L corresponding to the left lung is output to the display control unit 33 by the screen display control unit 35. Then, as illustrated in FIG. 11, instead of the examination location selection buttons 1R to 6R corresponding to the right lung, the examination location selection buttons 1L to 6L corresponding to the left lung are displayed in the second display region R2 by the display control unit 33 (Step S3).

The examination location selection buttons 1L to 6L are buttons for selecting one examination location as the examination target location from among six examination locations in the left lung.

Figure 11:
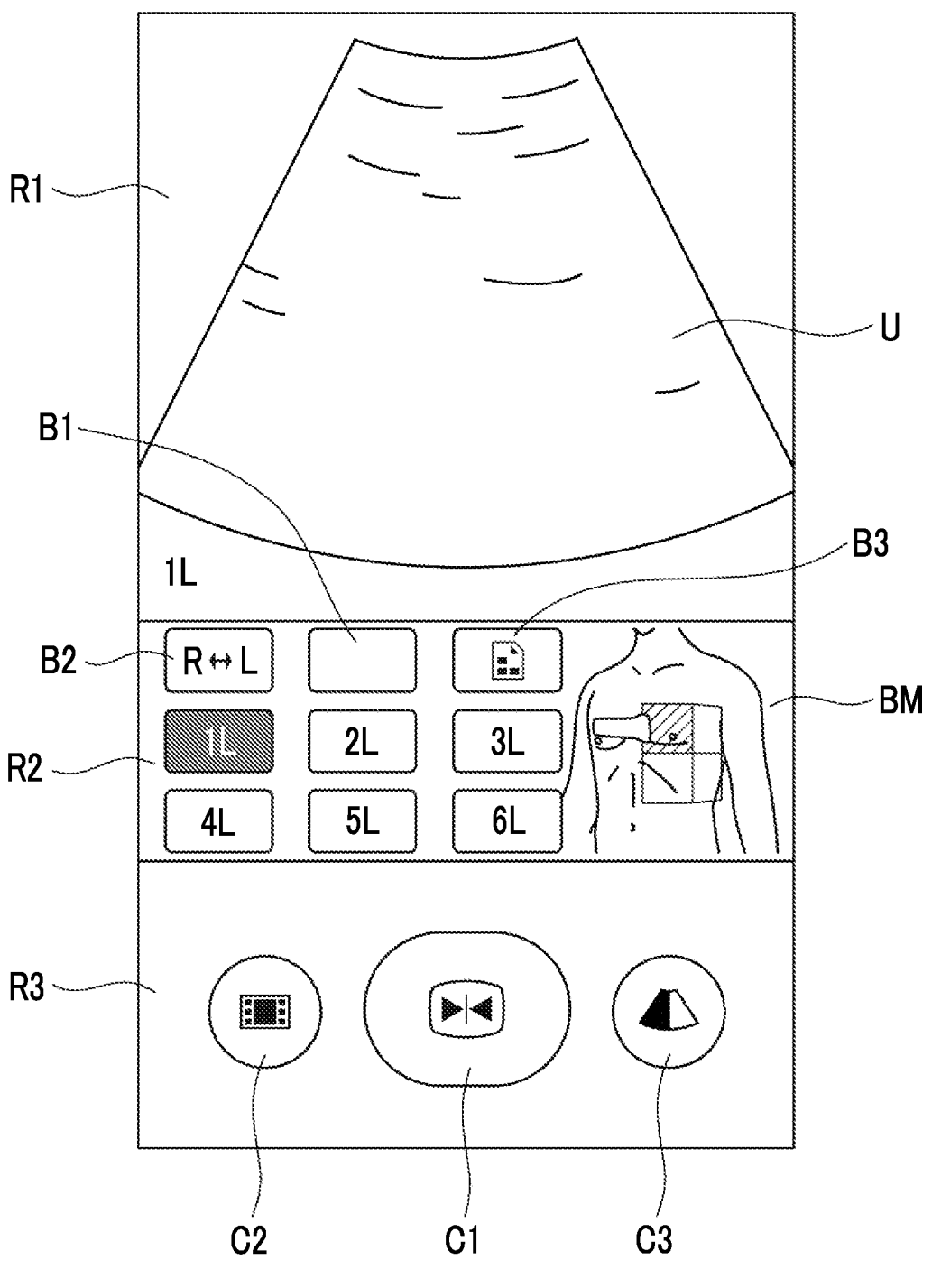
FIG. 11 is a conceptual diagram of an embodiment illustrating a display screen of a monitor in a case where an examination target is a left lung.

On the other hand, in a case where the examination target is a left lung, the examination location selection buttons 1L to 6L corresponding to the left lung are displayed in the second display region R2 by the display control unit 33, as illustrated in FIG. 11. In this state, in a case where the user taps and selects the left and right switching button B2, the examination target is switched from the left lung to the right lung, the data of the examination location selection buttons 1R to 6R corresponding to the right lung is output to the display control unit 33 by the screen display control unit 35. Then, as illustrated in FIG. 4, instead of the examination location selection buttons 1L to 6L corresponding to the left lung, the examination location selection buttons 1R to 6R corresponding to the right lung are displayed in the second display region R2 by the display control unit 33 (Step S3).

In this manner, in a case where one lung is switched to the other lung by the left and right switching button B2, the examination target is switched from the right lung to the left lung or from the left lung to the right lung, and instead of a plurality of examination location selection buttons of one lung, a plurality of examination location selection buttons of the other lung are displayed.

In a case where the examination target is switched from one lung to the other lung by the left and right switching button B2, instead of the body mark of one lung, a body mark in an orientation corresponding to the examination location of the other lung, indicating the examination location in the other lung is displayed on the monitor, and thereby the examination location of the lung can be displayed in an easy-to-understand manner on the display screen of the monitor 34 with a limited display region.

In the present embodiment, it is assumed that the examination target is switched to the right lung by the user.

Figure 12:
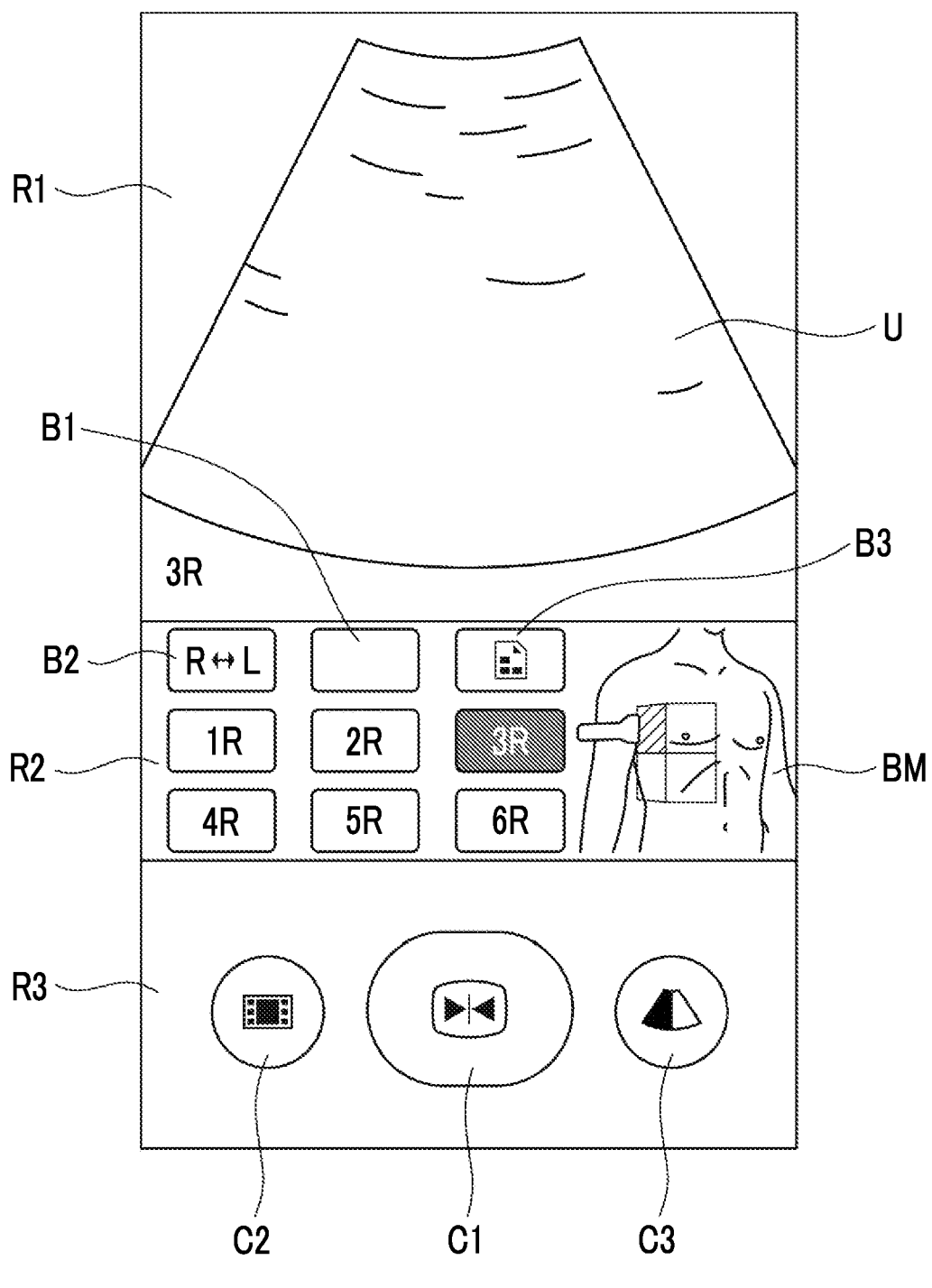
FIG. 12 is a conceptual diagram of an embodiment illustrating a display screen of a monitor in a case where an examination target location is an examination location 3R.

Here, in a case where the examination target location is the examination location 1R, the examination location selection button 1R is displayed in an emphasized manner by the display control unit 33, as illustrated in FIG. 4. Further, the body mark BM in an orientation corresponding to the examination location 1R is displayed, the examination location mark 1R is displayed in an emphasized manner, the probe mark PM is displayed in an orientation and at a position pointing the examination location mark 1R. In this state, in a case where the user taps and selects, for example, the examination location selection button 3R, the examination target location is switched from the examination location 1R to the examination location 3R, and the data of the body mark corresponding to the examination location 3R is output to the display control unit 33 by the screen display control unit 35. Then, instead of the examination location selection button 1R, the examination location selection button 3R is displayed in an emphasized manner by the display control unit 33, as illustrated in FIG. 12. Further, the body mark BM in an orientation corresponding to the examination location 3R is displayed, instead of the examination location mark 1R, the examination location mark 3R is displayed in an emphasized manner, the probe mark PM is displayed in an orientation and at a position pointing the examination location mark 3R instead of the examination location mark 1R (Step S4).

In this manner, by one examination location selection button selected from among a plurality of examination location selection buttons, the examination target location is switched to the examination location corresponding to the selected one examination location selection button, and the body mark BM in an orientation corresponding to one examination location, indicating the one examination location as the examination target location selected from among a plurality of examination locations. The probe mark PM is displayed in an orientation and at a position pointing the examination location mark corresponding to the selected examination location selection button.

As a result, the user can understand information required for the examination, such as the overall image of the torso including lungs, each examination location on the body mark BM, and the position and orientation in a case where the ultrasound probe 1 is brought into contact with the subject.

In the present embodiment, it is assumed that the examination location 1R is selected as the examination target location by the user.

In a case where the number of examination locations, the lung as the examination target, and the examination location as the examination target location are set as the initial setting (default), switching the number of examination locations, switching the lung as the examination target, and selecting the examination location are not essential. For example, in a case where the number of examination locations as the initial setting is six and the user desires six examination locations, switching the number of examination locations is not necessary. The same applies to switching of lungs as the examination target and the selection of the examination location. Further, the operation is similarly performed in a case where the number of examination locations is switched to four, in a case where the examination target is switched to the left lung, and in a case where the examination location other than the examination location 1R is selected as the examination target location.

Subsequently, the user brings the ultrasound probe 1 into contact with the location of the right lung of the subject corresponding to the examination location 1R by referring to the examination location 1R displayed by being superimposed on the body mark BM and the orientation and the position of the probe mark PM pointing the examination location 1R.

In this manner, in a case where a live mode is designated, the body mark BM including the probe mark PM is displayed on the monitor 34, and thereby the user can use the probe mark PM as a guide in a case of bringing the ultrasound probe 1 into contact with the location of the lung of the subject.

In this state, in a case where the transmission of the ultrasonic waves is started by the transmission and reception circuit 14 on the basis of the user's instruction input from the input device 37, sound ray signals are generated.

That is, the ultrasound beams are transmitted to the lung from a plurality of transducers of the transducer array 11 according to the drive signals from the pulser 51.

Ultrasound echoes from the lung based on the ultrasound beams transmitted from the pulser 51 are received by each transducer of the transducer array 11, and the reception signal as an analog signal is output from each transducer of the transducer array 11, which has received the ultrasound echo.

The reception signal as the analog signal output from each transducer of the transducer array 11 is amplified by the amplification unit 52, and is subjected to AD conversion by the AD conversion unit 53, and thereby the reception data is acquired.

By performing the reception focusing processing on the reception data by the beam former 54, the sound ray signal is generated.

Next, the ultrasound image (ultrasound image signal) U of the lung is generated by the image generation unit 31 on the basis of the sound ray signal generated by the beam former 54 of the transmission and reception circuit 14 (Step S5).

That is, the sound ray signal generated by the beam former 54 is subjected to various kinds of signal processing by the signal processing unit 16, and the image information data representing tomographic image information regarding tissues inside the subject is generated.

The image information data generated by the signal processing unit 16 is raster-converted by the DSC 18, and is further subjected to various kinds of image processing by the image processing unit 17, and thus the ultrasound image (ultrasound image signal) U is generated.

The ultrasound image U generated by the image processing unit 17 is held in the image memory 32.

Next, predetermined processing is performed on the ultrasound image U held in the image memory 32 by the display control unit 33, and the ultrasound image (video) U corresponding to the examination location 1R of the subject captured using the ultrasound probe 1 is displayed in the first display region R1 of the monitor 34 (Step S6).

As described above, by displaying the examination location number switching button B1, the left and right switching button B2, the examination location selection buttons 1R to 6R or 1L to 6L, the body mark BM, the ultrasound image U, and the like in one screen of the monitor 34, the user can check the number of necessary examination locations at once, and can collectively check the position and orientation in a case of bringing the ultrasound probe 1 into contact with the subject, and the ultrasound image at that time.

Subsequently, the user moves the ultrasound probe 1 within the region of the examination location 1R by referring to the ultrasound image U displayed on the monitor 34. In response, the ultrasound image U at a position to which the ultrasound probe 1 is moved is captured and displayed in the first display region R1 by the display control unit 33.

Subsequently, in a case where the user taps and selects the freeze button in the first display screen in a state where the desired ultrasound image U is displayed on the monitor 34, the ultrasound image (static image) U of the examination location 1R at a time point when the freeze button is selected is displayed in the first display region R1, and is held in the image memory 32 by the display control unit 33 (Step S7).

Further, in a case where the freeze button is selected, the data of the second display screen is output from the data of various display screens read out from the screen display memory 38, by the screen display control unit 35, and instead of the first display screen, the second display screen is displayed in the third display region R3 by the display control unit 33 (Step S8).

By switching the first display screen to the second display screen and displaying the second display screen in the third display region R3, the display screen of the monitor 34 with a limited display region can be efficiently used to display the display screen for operating the ultrasound diagnostic apparatus. Further, by switching the first display screen to the second display screen by selecting the freeze button instead of, for example, a second display screen switching button for switching the first display screen to the second display screen, it is possible to eliminate the trouble of selecting the second display screen switching button after selecting the freeze button, and to automatically switch the first display screen to the second display screen only by selecting the freeze button.

Figure 13:
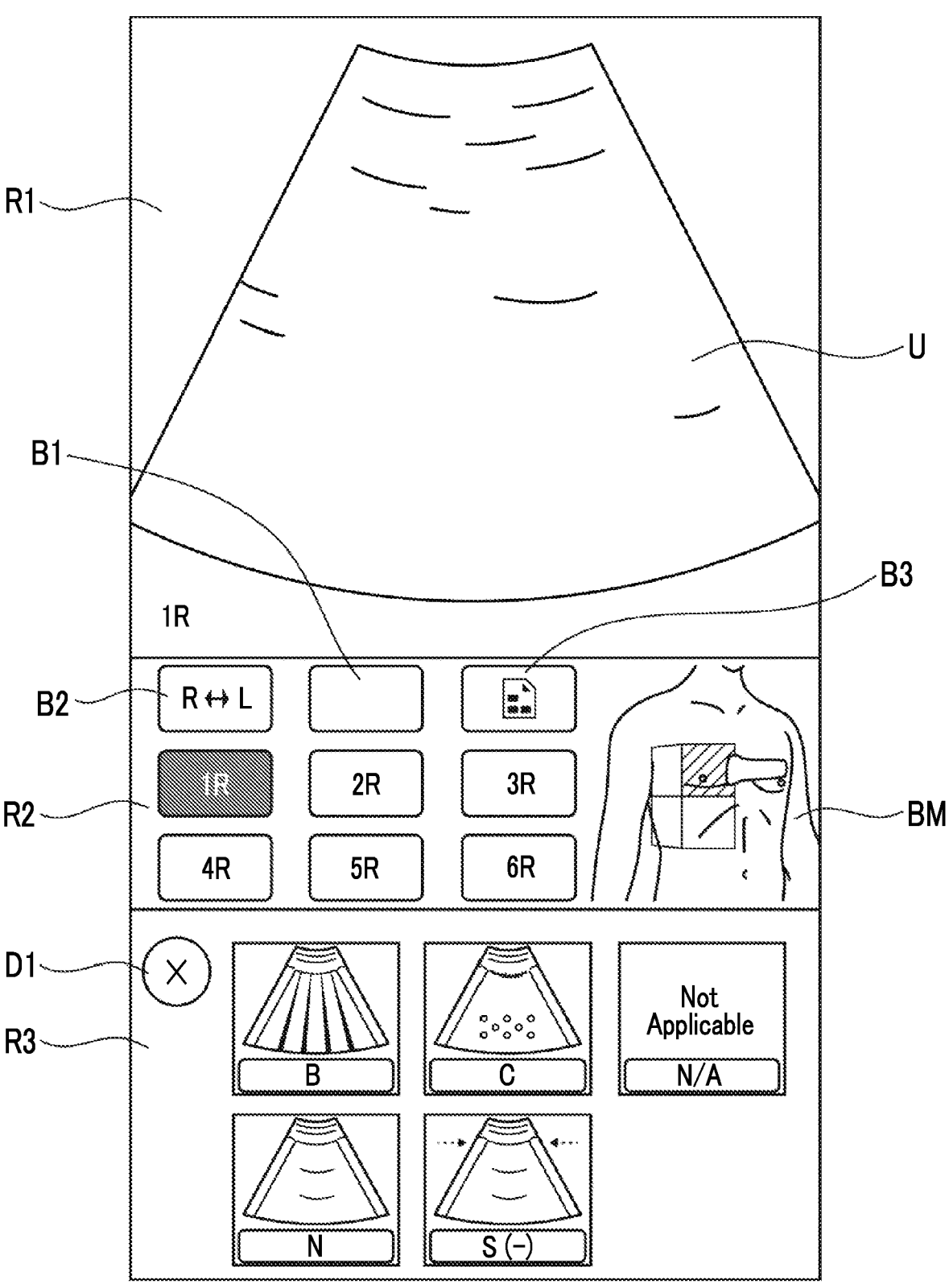
FIG. 13 is a conceptual diagram of an embodiment illustrating a second display screen.

FIG. 13 is a conceptual diagram of an embodiment illustrating a second display screen. The second display screen is a screen for inputting (selecting) the user's diagnostic findings for the examination target location of the lung, and includes a third display screen switching button D1 in addition to a plurality of diagnostic finding buttons corresponding to a plurality of predetermined diagnostic findings. In the present embodiment, the second display screen includes five diagnostic finding buttons B, C, N, S(–), and N/A corresponding to five diagnostic findings, as illustrated in FIG. 13.

The diagnostic finding button is an annotation button for adding the user's diagnostic findings to the ultrasound image of the examination target location, the diagnostic finding button B means B-lines, the diagnostic finding button C means consolidation, the diagnostic finding button N means normal, the diagnostic finding button S(–) means no lung sliding, and the diagnostic finding button N/A means not applicable. The types of diagnostic findings are not limited to five described above, and at least one of the plurality of diagnostic findings may include any one of the diagnostic findings of B-lines, consolidation, normal, or no lung sliding. Further, the number, arrangement order, and the like of the diagnostic findings are not limited, and diagnostic findings other than the above five diagnostic findings may be included.

The third display screen switching button D1 is a button for displaying the third display screen in the third display region R3 instead of the second display screen.

The plurality of diagnostic finding buttons have a design corresponding to the type of the ultrasound probe 1 connected to the diagnostic apparatus main body 3. In a case where the type of the ultrasound probe 1 connected to the diagnostic apparatus main body 3 is changed by the user while the second display screen is displayed in the third display region, the second display screen including a plurality of diagnostic finding buttons with a design according to the changed type of the ultrasound probe 1, instead of a plurality of diagnostic finding buttons being displayed, is displayed in the third display region R3 by the display control unit 33.

Figure 14A:
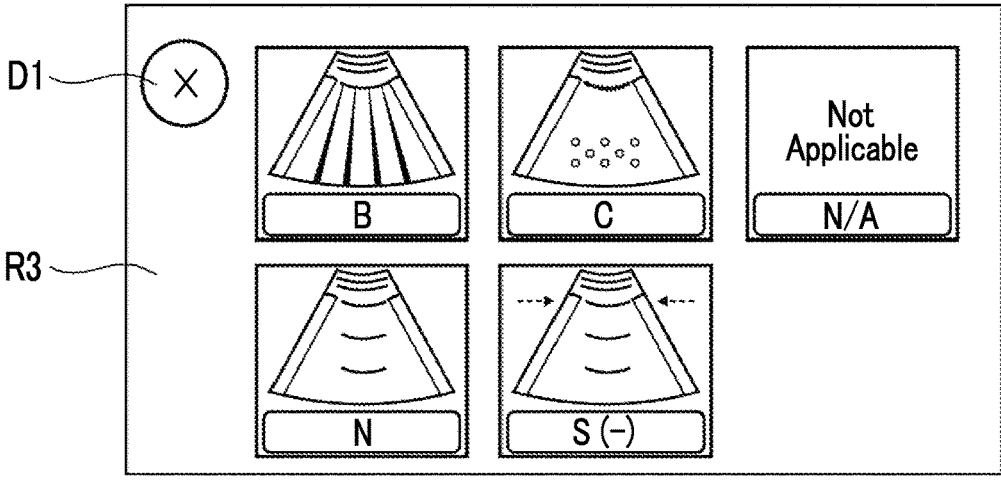
FIG. 14A is a conceptual diagram of an embodiment illustrating diagnostic finding buttons with a design according to the type of an ultrasound probe connected to a diagnostic apparatus main body.
Figure 14B:
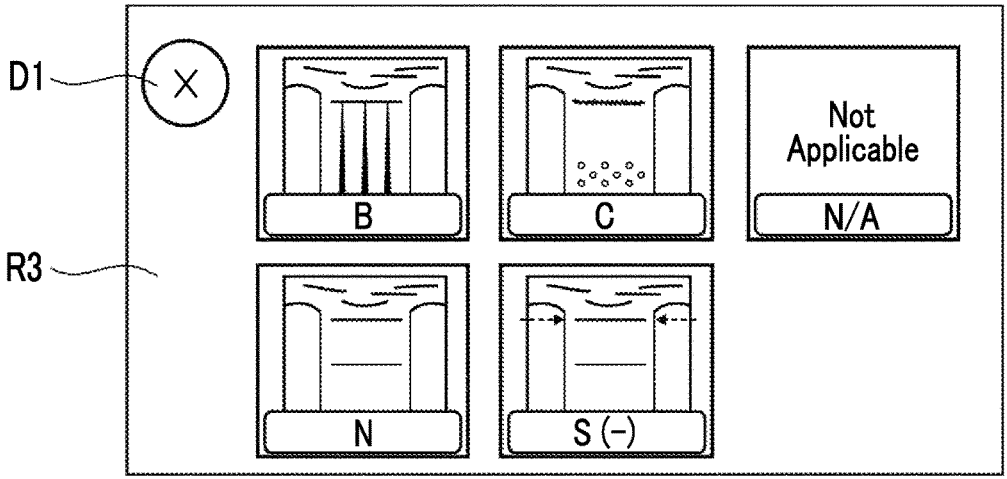
FIG. 14B is a conceptual diagram of an embodiment illustrating diagnostic finding buttons with a design according to the type of an ultrasound probe connected to a diagnostic apparatus main body.
Figure 14C:
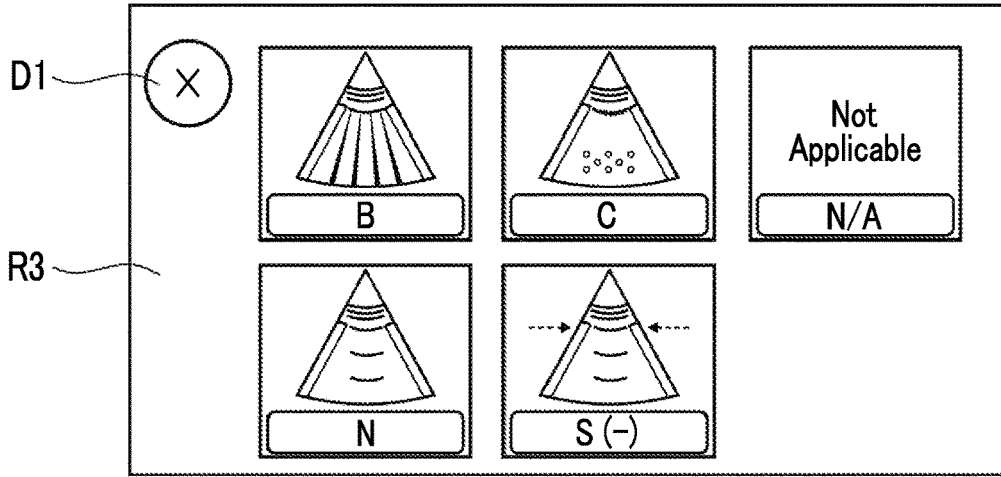
FIG. 14C is a conceptual diagram of an embodiment illustrating diagnostic finding buttons with a design according to the type of an ultrasound probe connected to a diagnostic apparatus main body.

FIGS. 14A, 14B, and 14C are conceptual diagrams of an embodiment illustrating diagnostic finding buttons with a design according to the type of the ultrasound probe 1 connected to the diagnostic apparatus main body 3, respectively. In a case where a convex type ultrasound probe 1 is connected to the diagnostic apparatus main body 3, as illustrated in FIG. 14A, the second display screen including the diagnostic finding buttons with a design according to the convex type ultrasound probe 1 is displayed in the third display region R3 by the display control unit 33.

Similarly, in a case where a linear type ultrasound probe 1 is connected to the diagnostic apparatus main body 3, the second display screen including the diagnostic finding buttons with a design according to the linear type ultrasound probe 1 is displayed in the third display region R3 as illustrated in FIG. 14B, and in a case where a sector type ultrasound probe 1 is connected to the diagnostic apparatus main body 3, the second display screen including the diagnostic finding buttons with a design according to the sector type ultrasound probe 1 is displayed in the third display region R3 as illustrated in FIG. 14C.

As a result, the user can understand the type of the ultrasound probe 1 being used by the design of the diagnostic finding buttons.

Subsequently, the user determines the symptoms by referring to the ultrasound image U displayed in the first display region R1, and taps and selects one diagnostic finding that matches the user's diagnostic finding, from among five diagnostic finding buttons included in the second display screen (Step S9).

As a result, the ultrasound image U, and the examination location 1R, the body mark BM, the diagnostic finding, and the like that correspond to the ultrasound image U are saved in the image memory 32 in association with each other.

In a case where one diagnostic finding selected from among a plurality of diagnostic findings is input for each examination location by one diagnostic finding button selected from among a plurality of diagnostic finding buttons, the diagnostic finding corresponding to one diagnostic finding button is displayed in the second display region R2 for each examination location mark by the display control unit 33.

Figure 15A:
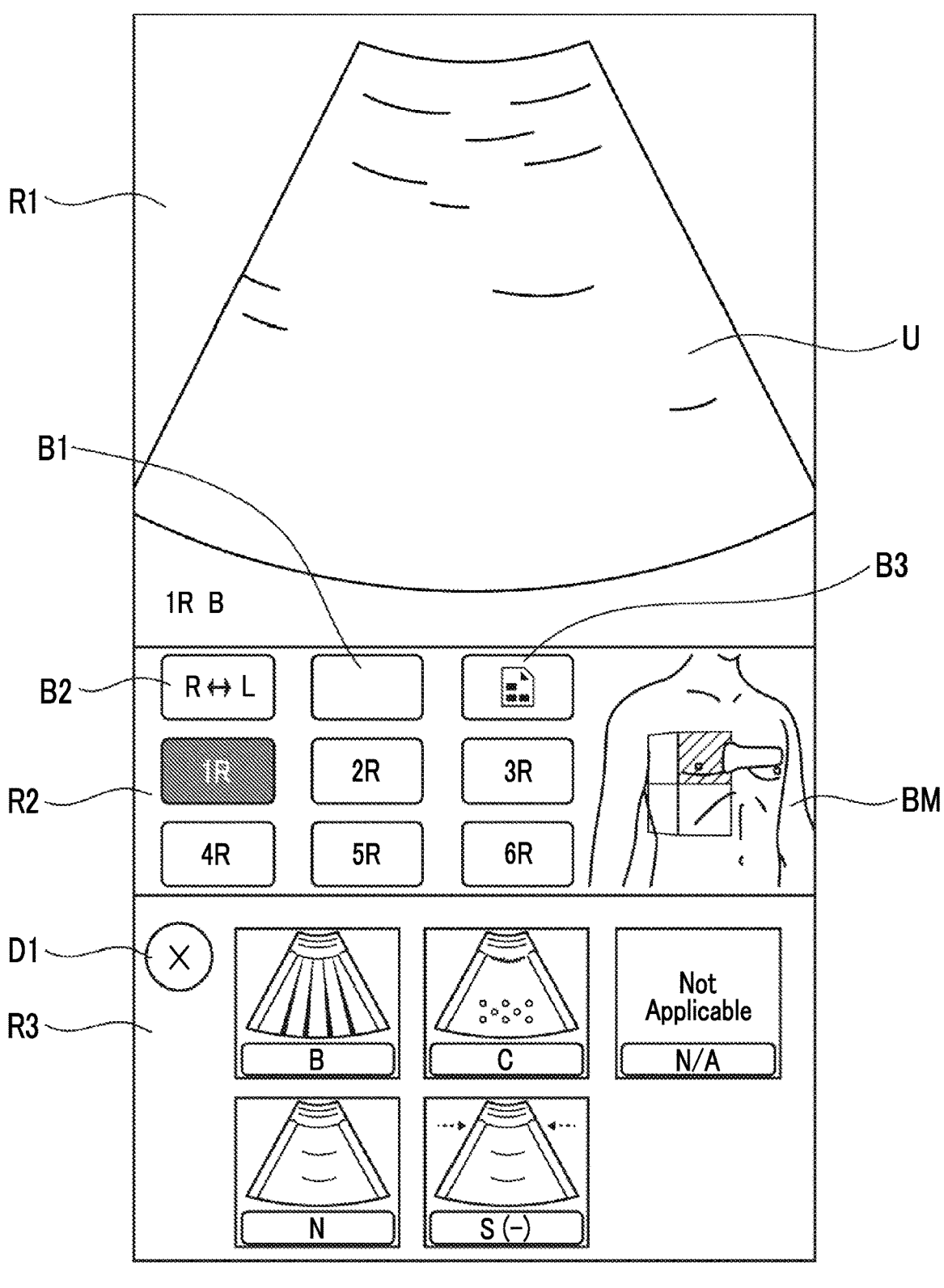
FIG. 15A is a conceptual diagram of an embodiment illustrating a display screen of a monitor in a case where a diagnostic finding B is input.
Figure 15B:
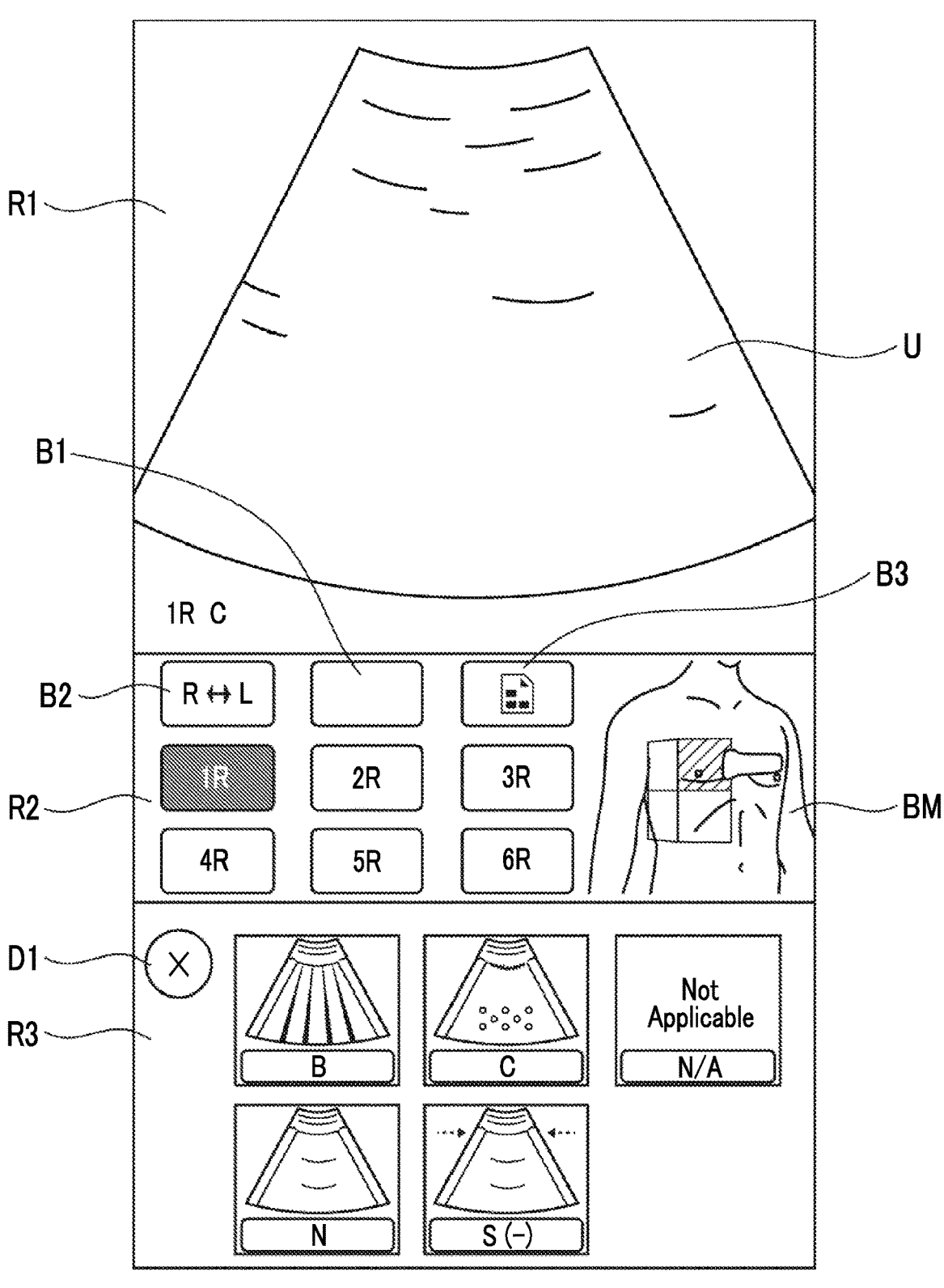
FIG. 15B is a conceptual diagram of an embodiment illustrating a display screen of a monitor in a case where a diagnostic finding B is input.

Furthermore, the ultrasound image U and one diagnostic finding input for the ultrasound image U are displayed in the first display region R1 by the display control unit 33. For example, in a case where the diagnostic finding button B is selected, as illustrated in FIG. 15A, "B" corresponding to the diagnostic finding button B is displayed on the right side of "1R" corresponding to the examination location selection button 1R displayed at the lower left portion of the first display region R1. In addition, in a case where the diagnostic finding button C is selected, as illustrated in FIG. 15B, "C" corresponding to the diagnostic finding button C is displayed on the right side of "1R" corresponding to the examination location selection button 1R displayed at the lower left portion of the first display region R1.

Instead of the user selecting the diagnostic finding button to manually input the diagnostic finding, a prediction result of the diagnostic finding of the lung included in the ultrasound image U may be automatically specified by using a determination model.

The determination model is a trained model that has learned, using learning ultrasound images of the lung of any subject as teacher data, a relationship between the learning ultrasound image and the diagnostic finding of the lung included in the learning ultrasound image, for a plurality of pieces of the teacher data.

The determination model uses the ultrasound image that is a determination target as an input, and outputs the prediction result of the diagnostic finding of the lung included in the ultrasound image on the basis of the training result.

Further, instead of the determination model, an image analysis unit that analyzes the ultrasound image may be provided, and the determination result of the diagnostic finding of the lung included in the ultrasound image may be output on the basis of an analysis result of the ultrasound image by the image analysis unit.

Subsequently, in a case where the user taps and selects the third display screen switching button D1 of the second display screen, the data of the third display screen from among the pieces of data of various display screens read out from the screen display memory 38 is output to the display control unit 33 by the screen display control unit 35. Then, instead of the second display screen, the third display screen is displayed in the third display region R3 by the display control unit 33 (Step S10).

Figure 16:
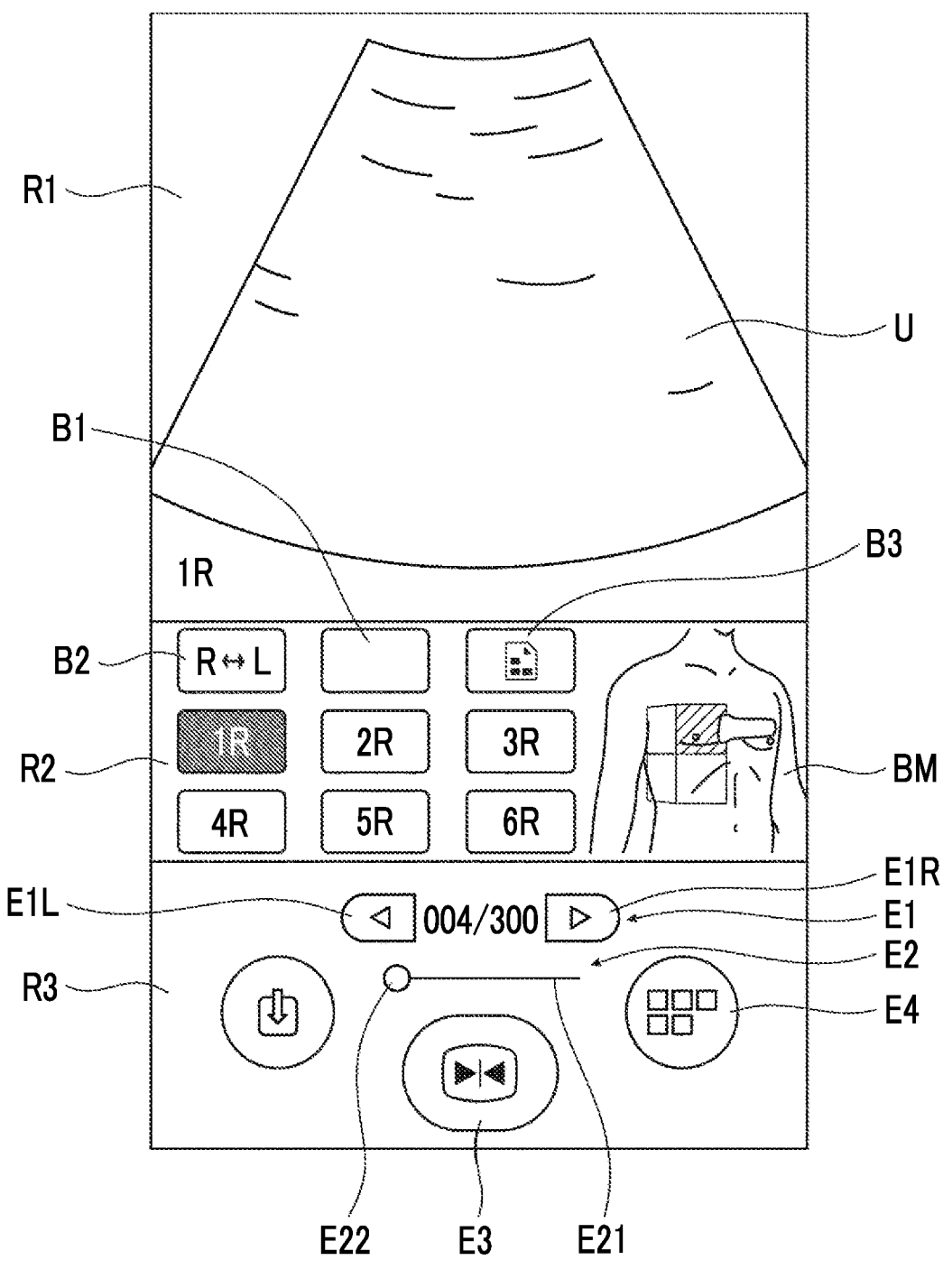
FIG. 16 is a conceptual diagram of an embodiment illustrating a third display screen.

FIG. 16 is a conceptual diagram of an embodiment illustrating a third display screen. The third display screen is a screen for selecting and saving an ultrasound image of one frame from among ultrasound images of a plurality of frames captured during a certain past period up to the time point of selecting the freeze button C1 of the first display screen, instead of the ultrasound image U saved at the time point of the user tapping and selecting the freeze button C1 of the first display screen, and includes a frame selection button E1, a frame slide bar E2, a freeze button E3, a second display screen switching button E4, and the like, as illustrated in FIG. 16.

The frame selection button E1 includes a left button E1L and a right button E1R. In a case where the user taps and selects the left button E1L or the right button E1R, the ultrasound image U is displayed in the first display region R1 frame by frame in the left direction (direction from the present to the past) or the right direction (direction from the past to the present) in a frame-advanced manner. Further, in a case where the user presses and holds the left button E1L or the right button E1R to select the left button E1L or the right button E1R, the frame of the ultrasound image U is fast-forwarded in the left direction or the right direction.

"004/300" indicates that the ultrasound image U being frame-advanced or fast-forwarded is the ultrasound image of the fourth frame among the ultrasound images of 300 frames.

The frame slide bar E2 includes a slide bar E21 and a slide knob E22. In a case where the user slides the slide knob E22 in the left direction or the right direction along the slide bar E21, the ultrasound image U is searched frame by frame in the left direction or the right direction, and is displayed in the first display region R1.

The freeze button E3 is a button for saving the ultrasound image of the frame selected using the frame selection button E1 or the frame slide bar E2 by the user, in the image memory 32, instead of the ultrasound image saved at the time point of the user tapping and selecting the freeze button C1 of the first display screen.

The second display screen switching button E4 is a button for returning from the third display screen to the second display screen and displaying the second display screen in the third display region R3 instead of the third display screen.

Subsequently, the user selects the ultrasound image of the desired frame among the ultrasound images of the plurality of frames by using the frame selection button E1 or the frame slide bar E2, and taps and selects the freeze button E3 of the third display screen. In response, instead of the ultrasound image saved at the time point of the user tapping and selecting the freeze button C1 of the first display screen, the ultrasound image of the selected desired frame is saved in the image memory 32.

In this manner, in a case where the user does not like the ultrasound image saved at the time of the user selecting the freeze button C1 of the first display screen, the user can select the ultrasound image of any desired one frame from among the ultrasound images of the plurality of past frames acquired up to the time point immediately before selecting the freeze button C1 of the first display screen.

Subsequently, in a case where the user taps and selects the report screen switching button B3 of the second display region R2, a report screen is created, and the data thereof is output to the display control unit 33 by the screen display control unit 35. Then, instead of the third display screen, the report screen is displayed on the monitor 34 by the display control unit 33 (Step S11).

Figure 17:
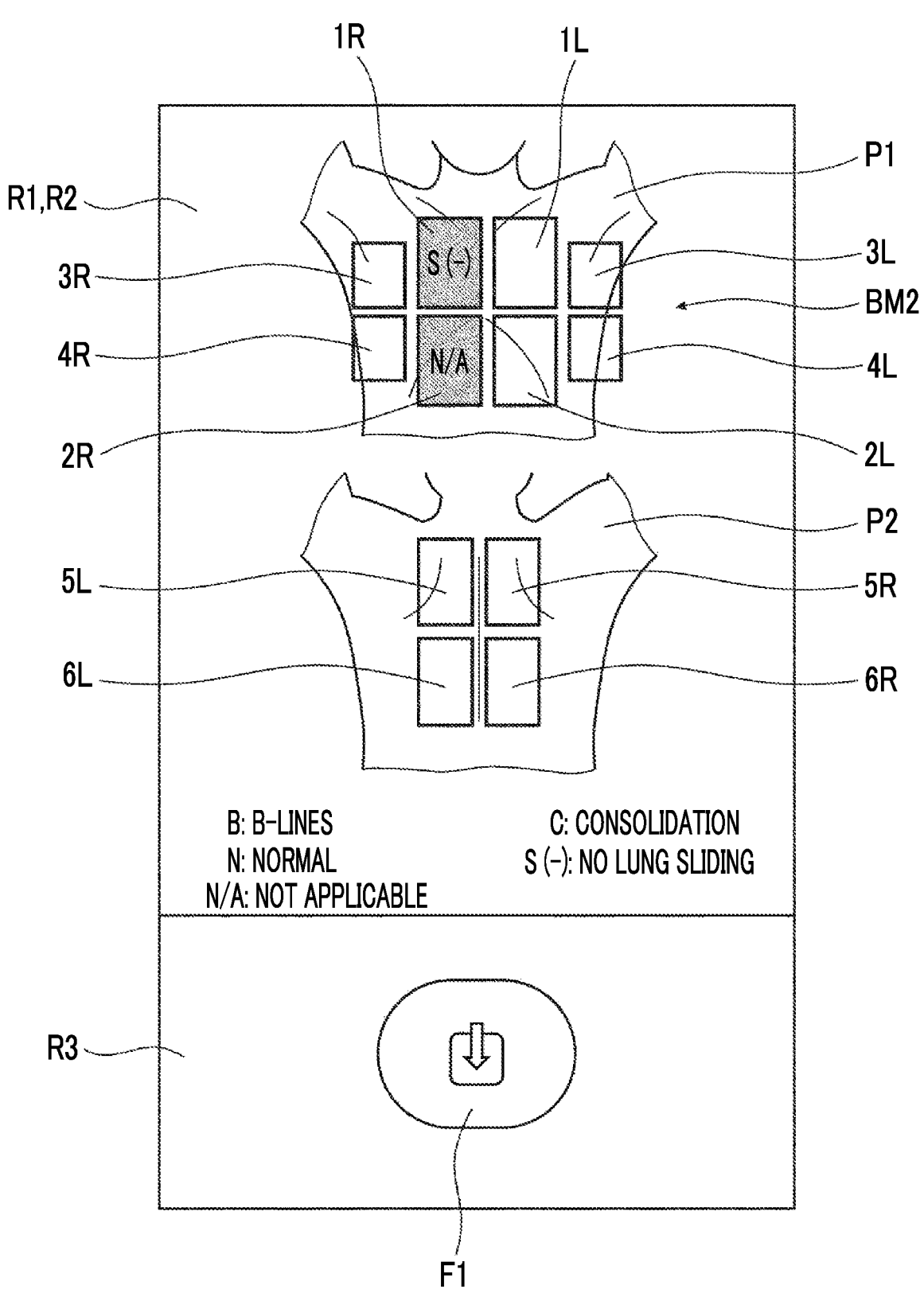
FIG. 17 is a conceptual diagram of an embodiment illustrating a report screen.

FIG. 17 is a conceptual diagram of an embodiment illustrating the report screen. The report screen is a screen collectively including the diagnostic findings input for the plurality of examination locations, and is displayed in the display region including the first display region R1, the second display region R2, and the third display region R3. As illustrated in FIG. 17, the report screen includes a diagnostic finding body mark BM2, and a save button F1. The diagnostic finding body mark BM2 is displayed in a display region including the first display region R1 and the second display region R2, and the save button F1 is displayed in a region including the third display region R3.

The diagnostic finding body mark BM2 indicates the examination location in both lungs of the subject, and includes schematic diagrams P1 and P2 on the front and back sides of the planar human body, the plurality of examination location marks 1R to 6R corresponding to the right lung, and the plurality of examination location marks 1L to 6L corresponding to the left lung, as illustrated in FIG. 17.

In the present embodiment, the schematic diagrams P1 and P2 on the front and back sides of the human body are schematic diagrams on the front and back sides of the torso part of the human body including the lungs, as illustrated in FIG. 17.

The plurality of examination location marks 1R to 6R and 1L to 6L are marks indicating a plurality of examination locations in the lungs of the schematic diagrams P1 and P2, and are displayed by being superimposed on the plurality of examination locations in the lungs of the schematic diagrams P1 and P2 of the human body.

In a case where the number of examination locations is six, as illustrated in FIG. 17, among six rectangular examination location marks 1R to 6R of the right lung and six rectangular examination location marks 1L to 6L of the left lung, four examination location marks 1R to 4R of the right lung and four examination location marks 1L to 4L of the left lung are displayed by being superimposed on the front-side schematic diagram P1, and two examination location marks 512 and 6R of the right lung and two examination location marks 5L and 6L of the left lung are displayed by being superimposed on the back-side schematic diagram P2.

In a case where the number of examination locations is four, the diagnostic finding body mark includes a schematic diagram on the front side of a planar human body, four pinpoint examination location marks 1R to 4R of the right lung, and four pinpoint examination location marks 1L to 4L of the left lung. Four pinpoint examination location marks 1R to 4R of the right lung and four pinpoint examination location marks 1L to 4L of the left lung are displayed by being superimposed on the front-side schematic diagram P1, for example.

In the example illustrated in FIG. 17, in the front-side schematic diagram P1, "S(–)" is displayed as the diagnostic finding in the rectangular region of the examination location mark 1R, and "N/A" is displayed as the diagnostic finding in the rectangular region of the examination location mark 2R. No diagnostic finding is displayed in the examination location mark for which the diagnostic finding is not input. The diagnostic finding is similarly displayed in the examination location mark for which the diagnostic finding is input, not only for the examination location marks 1R and 2R but also for the examination location marks 3R to 6R and 1L to 6L.

The save button F1 is a button for saving the information on the diagnostic finding in the image memory 32. Various buttons other than the save button F1 may be displayed in the display region of the save button.

By referring to the report screen, the user can save the trouble of selecting the examination locations one by one and checking the input diagnostic findings, and can collectively check the input diagnostic findings. The report screen can be displayed at any timing by the user tapping and selecting the report screen switching button B3.

In the same way, the user can switch the number of examination locations by the examination location number switching button B1, switch the lung as the examination target by the left and right switching button B2, and select again the examination location by the examination location selection button to continue the examination.

An examination location may be selected, and then an ultrasound image U of the examination location may be captured by using the ultrasound probe 1 by referring to the body mark BM of the examination location. Alternatively, the ultrasound image U may be captured by using the ultrasound probe 1, and then an examination location corresponding to the ultrasound image U may be selected. In any case, at a time point when the diagnostic finding is input for the ultrasound image U corresponding to the examination location, the ultrasound image U is associated with the examination location, the body mark, the diagnostic finding, and the like that correspond to the ultrasound image.

Next, the operation of the ultrasound diagnostic apparatus in the case of the freeze mode will be described.

In a case where the freeze mode is designated on the basis of the user's instruction input from the input device 37, the transmission of the ultrasonic waves from the transducer array 11 is stopped (Step S12).

Subsequently, the user switches the number of examination locations by the examination location number switching button B1, switches the lung as the examination target by the left and right switching button B2, and selects again the examination location of the examination target by the examination location selection button. In the present embodiment, it is assumed that the number of examination locations is switched to six, the examination target is switched to the right lung, and the examination location 1R is selected as the examination location of the examination target.

In this case, from among the ultrasound images of the plurality of past frames saved in the image memory 32 in association with the examination location 1R and the body mark BM, the ultrasound image of one frame in association with one examination location 1R selected from among the plurality of examination locations 1R to 6R by one examination location selection button 1R selected from among six examination location selection buttons 1R to 6R, the body mark BM, and the like are read out. Then, by the display control unit 33, the read-out ultrasound image is displayed in the first display region R1, and the read-out body mark BM and the like are displayed in the second display region R2 (Step S13).

As a result, the user can check the ultrasound image U by referring to the ultrasound image U displayed on the monitor 34. Further, it is possible to check the examination location and the like in a case where the ultrasound image U is captured, by referring to the examination location, and the orientation and position of the ultrasound probe, which are included in the body mark BM.

In a case where the freeze mode is selected, the body mark BM including the probe mark PM may be displayed on the monitor 34, or the body mark BM without the probe mark PM may be displayed on the monitor 34. The probe mark PM is displayed so that it is possible to check the orientation and position of the ultrasound probe 1 in the case of capturing the ultrasound image U even in a case where the users are different between the live mode and the freeze mode.

The ultrasound probe 1 and the diagnostic apparatus main body 3 may be connected in a wired or wireless manner. Further, the entire image generation unit 31 or only the signal processing unit 16 may be provided on the ultrasound probe 1 side, or provided on the diagnostic apparatus main body 3 side.

For example, in the apparatus of the present invention, the hardware configurations of the processing units executing various kinds of processing such as the transmission and reception circuit 14, the image generation unit 31, the display control unit 33, the screen display control unit 35, and the main body control unit 36 may be dedicated hardware, or may be various processors or computers that execute programs.

The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), and a dedicated electric circuit as a processor having a circuit configuration designed exclusively for executing specific processing such as an application specific integrated circuit (ASIC).

One processing unit may be configured by one of the various processors or may be configured by a combination of the same or different kinds of two or more processors, for example, a combination of a plurality of FPGAs or a combination of an FPGA and a CPU). Further, a plurality of processing units may be configured by one of various processors, or two or more of a plurality of processing units may be collectively configured by using one processor.

For example, there is a form where one processor is configured by a combination of one or more CPUs and software as typified by a computer, such as a server and a client, and this processor functions as a plurality of processing units. Further, there is a form where a processor fulfilling the functions of the entire system including a plurality of processing units by one integrated circuit (IC) chip as typified by a system on chip (SoC) or the like is used.

Furthermore, the hardware configurations of these various processors are more specifically electric circuitry where circuit elements, such as semiconductor elements, are combined.

The method of the present invention can be carried out, for example, by a program for causing a computer to execute each step of the method. Further, a computer-readable recording medium in which this program is recorded can also be provided.

The present invention has been described in detail, but the present invention is not limited to the above-described embodiments, and various improvements and changes may be made within a range not departing from the scope of the present invention.

EXPLANATION OF REFERENCES

1: ultrasound probe
3: diagnostic apparatus main body
11: transducer array
14: transmission and reception circuit
16: signal processing unit
17: image processing unit
18: DSC
32: image memory
33: display control unit
34: monitor
35: screen display control unit
36: main body control unit
37: input device
38: screen display memory
39: processor
51: pulser
52: amplification unit
53: AD conversion unit
54: beam former
R1: first display region
R2: second display region
R3: third display region
U: ultrasound image
B1: examination location number switching button
B2: left and right switching button
1R to 6R and 1L to 6L: examination location selection button
B3: report screen switching button BM: body mark
C1: freeze button
C2: video save button
C3: examination parameter setting button
D1: third display screen switching button
E1: frame selection button
E2: frame slide bar
E3: freeze button
E4: second display screen switching button
E1L: left button
E1R: right button
E21: slide bar
E22: slide knob
BM2: diagnostic finding body mark
F1: save button
P1, P2: schematic diagram

What is claimed is:

1. An ultrasound diagnostic apparatus comprising:
an ultrasound probe; and
a diagnostic apparatus main body connected to the ultrasound probe,
wherein the diagnostic apparatus main body includes
a monitor, and
a processor configured to
store in advance a plurality of diagnostic finding buttons corresponding to a plurality of predetermined diagnostic findings and having unique designs corresponding to each of a plurality of types of ultrasound probes,
display, on the monitor,
a first display region where ultrasound images of one lung of a subject continuously captured using the ultrasound probe are sequentially displayed,
a second display region including a plurality of examination location selection buttons for selecting one examination location as an examination target location from among a plurality of examination locations in the one lung, and
a third display region where a first display screen including a freeze button is displayed, and
wherein the processor is further configured to,
upon that the freeze button is selected,
keep displaying one ultrasound image captured when the freeze button is selected, on the first display region, and
display instead of the first display screen, a second display screen including only a plurality of diagnostic finding buttons having unique designs corresponding to the ultrasound probe connected to the diagnostic apparatus main body and a display screen switching button in the third display region, and
upon that the display screen switching button is selected,
display, instead of the second display screen, a display screen different from the second display screen.

2. The ultrasound diagnostic apparatus according to claim 1,
wherein the processor is further configured to display a body mark indicating the examination target location in the second display region.

3. The ultrasound diagnostic apparatus according to claim 1,
wherein at least one of the plurality of diagnostic findings includes any one of diagnostic findings of B-lines, consolidation, normal, or no lung sliding.

4. The ultrasound diagnostic apparatus according to claim 1,
wherein the processor is further configured to display, once a third display screen switching button is selected, instead of the second display screen, a third display screen for selecting an ultrasound image of one frame from among ultrasound images of a plurality of frames captured during a certain past period up to a time point of selecting the freeze button in the third display region.

5. The ultrasound diagnostic apparatus according to claim 4,
wherein the plurality of diagnostic finding buttons have a design according to a type of the ultrasound probe connected to the diagnostic apparatus main body, and
the processor is further configured to display, once the type of the ultrasound probe connected to the diagnostic apparatus main body is changed, instead of the plurality of diagnostic finding buttons being displayed, the second display screen including a plurality of diagnostic finding buttons with a design according to the changed type of the ultrasound probe in the third display region.

6. The ultrasound diagnostic apparatus according to claim 4,
wherein one diagnostic finding selected from among the plurality of diagnostic findings is input for each examination location by one diagnostic finding button selected from among the plurality of diagnostic finding buttons.

7. The ultrasound diagnostic apparatus according to claim 4,
wherein the processor is further configured to display a body mark indicating the examination target location in the second display region.

8. The ultrasound diagnostic apparatus according to claim 4,
wherein at least one of the plurality of diagnostic findings includes any one of diagnostic findings of B-lines, consolidation, normal, or no lung sliding.

9. The ultrasound diagnostic apparatus according to claim 1,
wherein the plurality of diagnostic finding buttons have a design according to a type of the ultrasound probe connected to the diagnostic apparatus main body, and
the processor is further configured to display, once the type of the ultrasound probe connected to the diagnostic apparatus main body is changed, instead of the plurality of diagnostic finding buttons being displayed, the second display screen including a plurality of diagnostic finding buttons with a design according to the changed type of the ultrasound probe in the third display region.

10. The ultrasound diagnostic apparatus according to claim 9,
wherein one diagnostic finding selected from among the plurality of diagnostic findings is input for each examination location by one diagnostic finding button selected from among the plurality of diagnostic finding buttons.

11. The ultrasound diagnostic apparatus according to claim 9,
wherein the processor is further configured to display a body mark indicating the examination target location in the second display region.

12. The ultrasound diagnostic apparatus according to claim 9,
wherein at least one of the plurality of diagnostic findings includes any one of diagnostic findings of B-lines, consolidation, normal, or no lung sliding.

13. The ultrasound diagnostic apparatus according to claim 1, wherein one diagnostic finding selected from among the plurality of diagnostic findings is input for each examination location by one diagnostic finding button selected from among the plurality of diagnostic finding buttons.

14. The ultrasound diagnostic apparatus according to claim 13,
wherein the processor is further configured to display a body mark indicating the examination target location in the second display region.

15. The ultrasound diagnostic apparatus according to claim 13,
wherein at least one of the plurality of diagnostic findings includes any one of diagnostic findings of B-lines, consolidation, normal, or no lung sliding.

16. The ultrasound diagnostic apparatus according to claim 13,
wherein the processor is further configured to display the ultrasound image, and the diagnostic finding input for the ultrasound image, in the first display region.

17. The ultrasound diagnostic apparatus according to claim 16,
wherein the processor is further configured to display, once a report screen switching button is selected, a report screen collectively including the diagnostic findings input for the plurality of examination locations, in a display region including the first display region, the second display region, and the third display region.

18. The ultrasound diagnostic apparatus according to claim 13,
wherein the processor is further configured to display, once a report screen switching button is selected, a report screen collectively including the diagnostic findings input for the plurality of examination locations, in a display region including the first display region, the second display region, and the third display region.

19. The ultrasound diagnostic apparatus according to claim 18,
wherein the report screen includes a diagnostic finding body mark, and
the diagnostic finding body mark includes a schematic diagram of a human body, and
an examination location mark that is displayed on the schematic diagram in a superimposed manner, and indicates the examination location.

20. A display method of an ultrasound diagnostic apparatus including an ultrasound probe, and a diagnostic apparatus main body connected to the ultrasound probe, the diagnostic apparatus main body including a monitor, the display method comprising:
storing in advance a plurality of diagnostic finding buttons corresponding to a plurality of predetermined diagnostic findings and having unique designs corresponding to each of a plurality of types of ultrasound probes;
displaying, on the monitor,
a first display region where ultrasound images of one lung of a subject continuously captured using the ultrasound probe are sequentially displayed,
a second display region including a plurality of examination location selection buttons for selecting one examination location as an examination target location from among a plurality of examination locations in the one lung, and
a third display region where a first display screen including a freeze button is displayed;
upon that the freeze button is selected,
keeping displaying one ultrasound image captured when the freeze button is selected, on the first display region; and
displaying instead of the first display screen, a second display screen including only a plurality of diagnostic finding buttons having unique designs corresponding to the ultrasound probe connected to the diagnostic apparatus main body a plurality of predetermined diagnostic findings and a display screen switching button in the third display region, and
upon that the display screen switching button is selected,
displaying, instead of the second display screen, a display screen different from the second display screen.

* * * * *